US012672988B2

(12) United States Patent
Van Ingelgem et al.

(10) Patent No.: US 12,672,988 B2
(45) Date of Patent: Jul. 7, 2026

(54) ABSORBENT ARTICLE WITH REDUCED ABSORBENT CORE

(71) Applicant: Drylock Technologies NV, Zele (BE)

(72) Inventors: Werner Van Ingelgem, Zele (BE); Steven Smet, Zele (BE); Bart Van Malderen, Zele (BE)

(73) Assignee: Drylock Technologies NV, Zele (BE)

( * ) Notice: Subject to any disclaimer, the term of this patent is extended or adjusted under 35 U.S.C. 154(b) by 1032 days.

(21) Appl. No.: 15/733,717

(22) PCT Filed: Apr. 4, 2019

(86) PCT No.: PCT/EP2019/058524
§ 371 (c)(1),
(2) Date: Oct. 2, 2020

(87) PCT Pub. No.: WO2019/193103
PCT Pub. Date: Oct. 10, 2019

(65) Prior Publication Data
US 2021/0015686 A1      Jan. 21, 2021

(30) Foreign Application Priority Data
Apr. 5, 2018   (EP) ..................................... 18165951

(51) Int. Cl.
*A61F 13/533*       (2006.01)
*A61F 13/49*        (2006.01)
(Continued)

(52) U.S. Cl.
CPC ........ *A61F 13/53* (2013.01); *A61F 13/49001* (2013.01); *A61F 13/511* (2013.01); (Continued)

(58) Field of Classification Search
CPC .............. A61F 13/4704; A61F 13/4756; A61F 13/49001; A61F 13/533; A61F 13/535; (Continued)

(56) References Cited

U.S. PATENT DOCUMENTS 5,891,118 A * 4/1999 Toyoshima ....... A61F 13/51305
604/382
10,517,775 B2 * 12/2019 Weisman ................ A61F 13/51
(Continued)

FOREIGN PATENT DOCUMENTS

EP        2627294 A1    8/2013
EP        2679210 A1    1/2014
(Continued)

OTHER PUBLICATIONS

"International Application Serial No. PCT/EP2019/058524, International Search Report mailed Jun. 3, 2019", (Jun. 19, 2019), 3 pgs.
(Continued)

*Primary Examiner* — Catharine L Anderson
(74) *Attorney, Agent, or Firm* — Schwegman Lundberg & Woessner, P.A.

(57) ABSTRACT

An absorbent article comprising a liquid pervious topsheet, a liquid impervious backsheet, and an absorbent core positioned between the liquid pervious topsheet and the liquid impervious backsheet; said absorbent article having a first and second longitudinal edge and a first and second transverse edge; wherein the absorbent core comprises a top core sheet, a back core sheet, and absorbent material arranged partially between the top core sheet and the back core sheet; wherein at least one of the top core sheet and the back core sheet comprises at least one attachment portion which is attached to the other one of the top core sheet and the back core sheet forming at least one attachment zone, and at least
(Continued)

one edge portion having at least one free edge and covering a portion of the absorbent material.

20 Claims, 13 Drawing Sheets

(51) Int. Cl.

| | |
|---|---|
| *A61F 13/511* | (2006.01) |
| *A61F 13/514* | (2006.01) |
| *A61F 13/53* | (2006.01) |
| *A61F 13/537* | (2006.01) |
| *A61F 13/539* | (2006.01) |

(52) U.S. Cl.
CPC ...................... *A61F 13/514* (2013.01); *A61F 2013/530051* (2013.01); *A61F 13/533* (2013.01); *A61F 13/53747* (2013.01); *A61F 2013/53908* (2013.01)

(58) Field of Classification Search
CPC .................. A61F 13/536; A61F 13/537; A61F 13/53747; A61F 2013/5315; A61F 2013/5355; A61F 2013/53908
See application file for complete search history.

(56) References Cited

U.S. PATENT DOCUMENTS

| | | | | |
|---|---|---|---|---|
| 11,065,159 | B2* | 7/2021 | Morita | ................ A61F 13/5125 |
| 11,123,235 | B2* | 9/2021 | Bianchi | ............. A61F 13/51113 |
| 2006/0004334 | A1 | 1/2006 | Schlinz et al. | |
| 2008/0312628 | A1 | 12/2008 | Hundorf et al. | |
| 2012/0089106 | A1* | 4/2012 | Komatsu | ............ A61F 13/4756 |
| | | | | 604/367 |
| 2016/0045397 | A1 | 2/2016 | Hironaga et al. | |

FOREIGN PATENT DOCUMENTS

| | | | |
|---|---|---|---|
| EP | 2901982 | A1 | 8/2015 |
| JP | 2013052161 | A | 3/2013 |
| WO | WO-2012052173 | A1 | 4/2012 |
| WO | WO-2015094732 | A1 | 6/2015 |
| WO | WO-2017087158 | A1 | 5/2017 |

OTHER PUBLICATIONS

"International Application Serial No. PCT/EP2019/058524, Written Opinion mailed Jun. 3, 2019", (Jun. 19, 2019), 6 pgs.

* cited by examiner

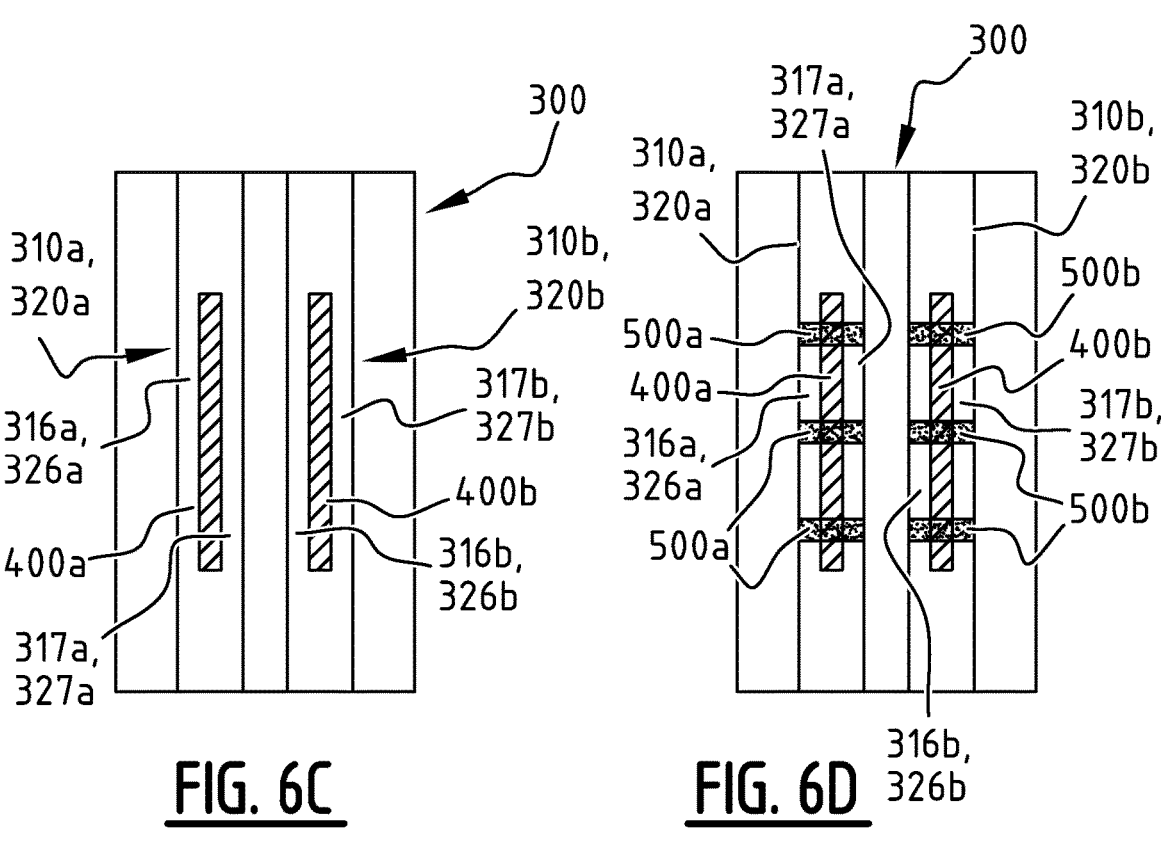
FIG. 6C            FIG. 6D
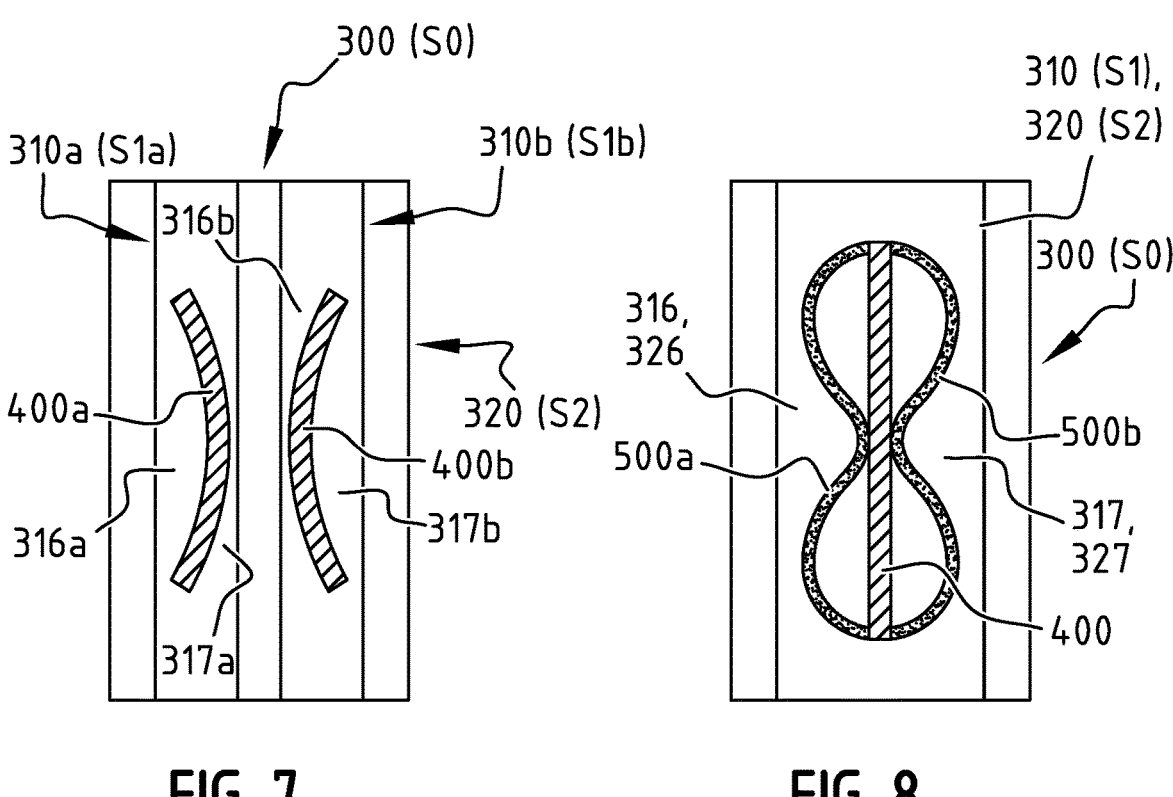
FIG. 7            FIG. 8

ABSORBENT ARTICLE WITH REDUCED ABSORBENT CORE

PRIORITY APPLICATIONS

This application is a U.S. National Stage Filing under 35 U.S.C. § 371 from International Application No. PCT/EP2019/058524, filed on Apr. 4, 2019, and published as WO2019/193103 on Oct. 10, 2019, which claims the benefit of priority to European Application No. 18165951.7, filed on Apr. 5, 2018; the benefit of priority of each of which is hereby claimed herein, and which applications and publication are hereby incorporated herein by reference in their entireties.

TECHNICAL FIELD

The present invention pertains to the technical field of absorbent articles, more preferably disposable personal care articles such as diapers, baby pants, adult incontinent garments, and the like, and to absorbent structures for use in such absorbent articles. More specifically the present invention relates to an absorbent structure comprising an absorbent core between a topsheet and a backsheet. The present invention also relates to a method and apparatus for manufacturing such an absorbent article.

BACKGROUND

Disposable absorbent articles have an absorbent structure for absorbing bodily exudates, a soft liquid-permeable topsheet on the wearer side and a liquid-impermeable backsheet on the garment side. The absorbent structure in between is normally made from a mixture of cellulose fibers or other fibrous substance and an absorbent polymer material. These fibrous substances make these absorbent articles typically quite fluffy and bulky.

In recent years there has been increasing demand for flexible, thinner, lightweight absorbent structures to resolve various problems of manufacturing, marketing, design, fit, wearing comfort, distribution, garbage disposal, material and energy consumption, transportation and storage costs and the like.

The most common method currently used to meet these demands in disposable absorbent articles is to reduce the amount of cellulose fibre or other support material within and surrounding the absorbent structure and/or use larger amounts of absorbent polymer materials. Consequently such absorbent articles have a smaller proportion of hydrophilic cellulose fibres and/or a higher proportion of absorbent polymers materials. Some of these absorbent articles may be better at storing liquid, however they are not necessarily good at absorbing and distributing liquid when the absorbent article is actually being used. It will thus be apparent from the above that the absolute and relative proportions of the fibrous material and absorbent polymer material are closely linked in light of article performance.

In order to obtain good absorbency, distribution and retention within such absorbent structures it has found to be important to at least partially immobilize the absorbent material. Failing to provide sufficient structural integrity results in loss of functional performance characteristics such as coherence, absorption, distribution and/or retention and results in failures related but not limited to for instance leakages, high rewet values, etc.

EP 2 627 294 relates to a method and apparatus for forming a composite structure, preferably for use in an absorbent structure used within the personal hygiene industry, such as for instance feminine hygiene garments, baby diapers and pants and adult incontinence garments. The invention preferably provides a method and apparatus for depositing and positioning particulate materials in a desired pattern onto a moving carrier layer. The method allows accurate forming of a pattern of particulate material clusters at high production speed having improved attachment properties, with reduced raw material usage and relative low cost.

WO 2012/052173 relates to a method and apparatus for forming a composite structure, preferably for use in an absorbent structure used within the personal hygiene industry, such as for instance feminine hygiene garments, baby diapers and pants and adult incontinence garments. The method comprises depositing particulate material in a desired pattern onto a moving carrier layer and positioning it into a pocketing pattern. The method allows accurate forming of a pre-determined pattern of particulate material clusters at high production speed, with reduced raw material usage and relative low cost. As such method allows manufacturing of absorbent structures being substantially cellulose free and substantially glue free, considered technically, economically and environmentally friendly.

There is a need in the art for an improved thin, flexible, lightweight absorbent structure which is discreet, sustainable and/or relatively inexpensive taking in mind manufacturing, marketing, design, fit, comfort, distribution, packaging, disposal, material, energy and transportation costs while preserving the required fluid absorption, distribution, transport, coherence and retention properties. There is furthermore also a need for a method and apparatus to produce such absorbent structures at high production speed and low energy and raw material consumption.

SUMMARY

The object of embodiments of the invention is to provide an absorbent article of the type stated in the preamble, with reduced manufacturing cost, light weight, thin, and good liquid distribution and absorption capacities.

According to a first aspect of the invention, there is provided an absorbent article comprising a liquid pervious topsheet, a liquid impervious backsheet, and an absorbent core positioned between the liquid pervious topsheet and the liquid impervious backsheet. The absorbent article has a first and second longitudinal edge and a first and second transverse edge. The absorbent core comprises a top core sheet, a back core sheet, and absorbent material arranged partially between the top core sheet and the back core sheet. At least one of the top core sheet and the back core sheet comprises at least one attachment portion which is attached to the other one of the top core sheet and the back core sheet forming at least one attachment zone, and at least one edge portion having at least one free edge and covering a portion of the absorbent material.

By providing at least one of the top core sheet and the back core sheet with at least one edge portion having at least one free edge and covering a portion of the absorbent material, the at least one of the top core sheet and the back core sheet does not cover the entire top and/or bottom surface of the absorbent material, resulting in less raw material needed for the absorbent core. The at least one attachment portion forms at least one attachment zone capable of creating a channel for liquid distribution and absorption upon wetting. In this manner, at least one channel can be created with a reduced amount of material used for manufacturing the top core sheet and/or back core sheet, and as a result the manufacturing cost can be reduced while good liquid distribution and absorption capacities can be maintained. In addition, the thickness and weight of absorbent article may be reduced.

It is noted that either the top core sheet or the back core sheet may have a free edge and hence a reduced surface area compared to an absorbent core of the prior art which fully wraps the absorbent material, or both the top core sheet and the back core sheet may have a free edge.

In an exemplary embodiment, seen in a top view of the absorbent core, the top core sheet has a total surface area of S1, the back core sheet has a total surface area of S2, the absorbent core has a surface area of S0 defined by an area covered by the absorbent material plus an area of the at least one attachment zone, wherein S1 is smaller than 90% of S0 and/or S2 is smaller than 90% of S0.

In an exemplary embodiment, S1 and/or S2 is smaller than 80% of S0, preferably S1 and/or S2 is smaller than 70% of S0, more preferably S1 and/or S2 is smaller than 60% of S0, even more preferably S1 and/or S2 is smaller than 50% of S0, most preferably S1 and/or S2 is smaller than 40% of S0.

In an exemplary embodiment, in the at least one attachment zone substantially no absorbent material is present between the top core sheet and the back core sheet, preferably the at least one attachment zone is a continuous zone with substantially no absorbent material arranged between the top core sheet and the back core sheet, which allows the formation of at least one channel upon wetting and hence a better liquid distribution throughout the absorbent core, enabling better liquid absorbance.

In an exemplary embodiment, the at least one edge portion comprises a first edge portion and a second edge portion located at opposite sides of the at least one attachment portion. This provides a stable structural basis for the formation of channel after the absorbent core is wetted, and results in the formation of tubes which provide a tub shape to the absorbent core.

In an exemplary embodiment, the at least one attachment zone comprises an attachment zone extending from a crotch region in the direction of the first and/or second transverse edge of the absorbent core, and/or an attachment zone extending in the direction from the first longitudinal edge to the second longitudinal edge of the absorbent core. It allows a better liquid distribution between crotch region and front and/or back portion of absorbent article, and/or between left and right portions of absorbent article.

In an exemplary embodiment, the top core sheet and/or the back core sheet has a substantially rectangular shape.

In an exemplary embodiment, the top core sheet and/or the back core sheet has a longitudinal dimension which is at least 20% of a length of the absorbent core, preferably at least 30%, more preferably at least 50%, even more preferably substantially 100% of the length of the absorbent core, which allows formation of a longer channel over a larger longitudinal dimension of the absorbent core and a better liquid distribution over the absorbent core.

In an exemplary embodiment, the top core sheet and/or the back core sheet has a transverse dimension which is at least 5% of a width of the absorbent core, preferably at least 10%, more preferably at least 20%, which allows a better liquid distribution over a larger transverse dimension of the absorbent core.

In an exemplary embodiment, a longitudinal dimension of the top core sheet and/or the back core sheet and the length of the absorbent core are within ±10% difference, preferably substantially the same. It allows an attachment between the top core sheet and the back core sheet by the first and second transverse edge of the absorbent core, providing a stable structure of the absorbent core while the use of material can still be reduced.

In an exemplary embodiment, a transverse dimension of the top core sheet and/or a transverse dimension of the back core sheet and the width of the absorbent core are within ±10% difference, preferably substantially the same. It allows an attachment between the top core sheet and the back core sheet by the first and second longitudinal edge of the absorbent core, providing a stable structure of the absorbent core while the use of material can still be reduced.

In an exemplary embodiment, a rear and front edge of the top core sheet is attached to a rear and front edge of the back core sheet, respectively, providing a more stable structure of the absorbent core while the use of material can still be reduced.

In an exemplary embodiment, the absorbent article further comprises a second top core sheet comprising at least one second attachment portion which is attached to the back core sheet forming at least one second attachment zone, and at least one second edge portion having at least one free edge and covering a portion of the absorbent material. In this manner, a second channel can be created with a reduced amount of material for manufacturing both the top core sheet and back core sheet, as a result the liquid distribution and absorption capacities of the absorbent core is further improved with a reduced manufacturing cost.

In an exemplary embodiment, the absorbent article further comprising a second top core sheet and a second back core sheet, said second top core sheet comprising at least one second attachment portion which is attached to the second back core sheet forming at least one second attachment zone, and at least one second edge portion having at least one free edge and covering a portion of the absorbent material. In this manner, a second channel can be created with a reduced amount of material for manufacturing both the top core sheet and back core sheet, as a result the liquid distribution and absorption capacities of the absorbent core is further improved with a reduced manufacturing cost.

In an exemplary embodiment, the absorbent article further comprising a second back core sheet, said second back core sheet comprising at least one second attachment portion which is attached to the top core sheet forming at least one second attachment zone, and at least one second edge portion having at least one free edge and covering a portion of the absorbent material. In this manner, a second channel can be created with a reduced amount of material for manufacturing the back core sheet, as a result the liquid.

In an exemplary embodiment, a distance between the top core sheet and the second top core sheet is at least 5% of the width of the absorbent core, which allows a sufficient manufacturing cost reduction.

In an exemplary embodiment, a distance between the back core sheet and the second back core sheet is at least 5% of the width of the absorbent core, which allows a sufficient manufacturing cost reduction.

In an exemplary embodiment, the at least one attachment zone comprises at least one first attachment zone and at least one second attachment zone, which allows the creation of at least two channels using the at least one of the top core sheet and the back core sheet. In this manner the quantity of liquid that can be temperately held is further increased. In addition, as the total area of the attachment increases accordingly, and the liquid can be more evenly distributed over the entire absorbent core.

In an exemplary embodiment, said at least one first and second attachment zones extend next to each other from the crotch region in the direction of the first and/or the second transverse edge, which allows a better liquid distribution between crotch region and front and/or back portion of absorbent article.

In an exemplary embodiment, said at least one first and second attachment zones are connected through at least one semi-permanent attachment zone, preferably extending in a substantially transverse direction, so that liquid can flow in a transverse direction through the absorbent material of the absorbent core.

In an exemplary embodiment, the absorbent article further comprises adhesive between the absorbent core and the liquid pervious topsheet.

In an exemplary embodiment, the absorbent article further comprises an acquisition and distribution layer ADL, positioned between the absorbent core and the liquid pervious topsheet. This serves to slow down the flow so that the liquid has adequate time to be absorbed by and evenly distributed over the absorbent core.

In an exemplary embodiment, the absorbent article comprises adhesive between the absorbent core and the ADL, and/or the absorbent article comprises adhesive between the ADL and the liquid pervious topsheet.

In an exemplary embodiment, the at least one attachment zone has a center line, preferably the center line is a straight line, or a curve, or a polyline.

In an exemplary embodiment, the at least one attachment zone comprises a plurality of attachments zones which have substantially no absorbent material between the top core sheet and the back core sheet, and wherein absorbent material is present in an area in-between said plurality of attachment zones, between the top core sheet and the back core sheet.

In an exemplary embodiment, a contour of the or each attachment zone is adjacent to absorbent material.

In an exemplary embodiment, a length of the or each attachment zone is larger than 10% of the length of the absorbent core, more preferably larger than 30%, even more preferably larger than 50%, which allows a better liquid distribution over a large area of the absorbent core.

In an exemplary embodiment, said at least one attachment zone comprises at least one permanent attachment zone which remains attached when wetted, which allows the channel to distribute liquid during further liquid insults.

In an exemplary embodiment, the absorbent material comprises cellulosic fluff pulp and/or superabsorbent particles.

According to a second aspect of the invention, there is provided a method for manufacturing an absorbent article. The method comprising:

preparing a absorbent core by providing a top core sheet and a back core sheet, and by arranging absorbent material partially between the top core sheet and the back core sheet. The top core sheet is attached to the back core sheet forming at least one attachment zone, and the attaching is such that at least one of the top core sheet and the back core sheet has at least one edge portion having at least one free edge and covering a portion of the absorbent material; and including the absorbent core between a liquid pervious topsheet and a liquid impervious backsheet.

By attaching the top core sheet and the back core sheet such that at least one of the top core sheet and the back core sheet has at least one edge portion having at least one free edge and covering a portion of the absorbent material, the at least one of the top core sheet and the back core sheet does not cover the entire top and/or bottom surface of the absorbent material, and may be only located where the at least one attachment portion is formed to create a channel for liquid distribution and absorption upon wetting. In this manner, at least one channel can be created with a reduced amount of material used for manufacturing the top core sheet and/or back core sheet, and as a result the manufacturing cost can be reduced while good liquid distribution and absorption capacities can be maintained. In addition, the thickness and weight of the absorbent article may be reduced.

In an exemplary embodiment, the top core sheet and the back core sheet are fed continuously in a transport direction in the form of a web top core material and a web back core material having a first width and a second width, seen in a direction perpendicular on the transport direction, respectively; wherein the absorbent material is arranged such that, seen in a direction perpendicular on the transport direction, a distance between outer limits of absorbent material is $w0$, wherein the distance $w0$ is larger than the first and/or the second width, preferably at least 10% larger, more preferably at least 20% larger, even more preferably at least 40% larger.

In an exemplary embodiment, in the at least one attachment zone substantially no absorbent material is arranged between the top core sheet and the back core sheet, preferably the at least one attachment zone is a continuous zone with substantially no absorbent material arranged between the top core sheet and the back core sheet, which allows a better liquid distribution throughout the entire channel of the absorbent core, enabling better liquid absorbance.

In an exemplary embodiment, the attaching is such that the at least one edge portion comprises a first edge portion and a second edge portion located at opposite sides of the at least one attachment portion. This provides a stable structural basis for the formation of channel after the absorbent core is wetted, and results in the formation of tubes which provide a tub shape to the absorbent core.

In an exemplary embodiment, a rear and front edge of the top core sheet is attached to a rear and front edge of the back core sheet, respectively, providing a more stable structure of the absorbent core while the use of material can still be reduced.

In an exemplary embodiment, the method further comprising providing a second top core sheet and arranging absorbent material partially between the second top core sheet and the back core sheet; wherein the second top core sheet is attached to the back core sheet forming at least one second attachment zone, and the attaching is such that the second top core sheet has at least one second edge portion having at least one free edge and covering a portion of the absorbent material. In this manner, a second channel can be created with a reduced amount of material for manufacturing the top core sheet, as a result the liquid distribution and absorption capacities of the absorbent core is further improved with a reduced manufacturing cost.

In an exemplary embodiment, the method further comprising providing a second top core sheet and a second back core sheet and arranging absorbent material partially between the second top core sheet and the second back core sheet; wherein the second top core sheet is attached to the second back core sheet forming at least one second attachment zone, and the attaching is such that the second top core sheet has at least one second edge portion having at least one free edge and covering a portion of the absorbent material. In this manner, a second channel can be created with a reduced amount of material for manufacturing both the top core sheet and back core sheet, as a result the liquid distribution and absorption capacities of the absorbent core is further improved with a reduced manufacturing cost.

In an exemplary embodiment, the method further comprising providing a second back core sheet and arranging absorbent material partially between the top core sheet and the second back core sheet; wherein the top core sheet is attached to the second back core sheet forming at least one second attachment zone, and the attaching is such that the second back core sheet has at least one second edge portion having at least one free edge and covering a portion of the absorbent material. In this manner, a second channel can be created with a reduced amount of material for manufacturing the back core sheet, as a result the liquid distribution and absorption capacities of the absorbent core is further improved with a reduced manufacturing cost.

In an exemplary embodiment, the providing is such that a distance $d1$ between the top core sheet and the second top core sheet is at least 5% of the width of the absorbent core, which allows a sufficient manufacturing cost reduction.

In an exemplary embodiment, the providing is such that a distance $d2$ between the back core sheet and the second back core sheet is at least 5% of the width of the absorbent core, which allows a sufficient manufacturing cost reduction.

In an exemplary embodiment, the attaching is such that the at least one attachment zone comprises at least one first attachment zone and at least one second attachment zone, which allows the creation of at least two channels using the at least one of the top core sheet and the back core sheet. In this manner the quantity of liquid that can be temperately held is further increased. In addition, as the total area of the attachment increases accordingly, and the liquid can be more evenly distributed over the entire absorbent core.

In an exemplary embodiment, the attaching is such that the at least one first and second attachment zones extend next to each other from the crotch region in the direction of the first and/or the second transverse edge, which allows a better liquid distribution between crotch region and front and/or back portion of absorbent article.

In an exemplary embodiment, the attaching is such that the at least one first and second attachment zones are connected through at least one semi-permanent attachment zone, preferably extending in a substantially transverse direction, so that liquid can flow in a transverse direction through the absorbent material of the absorbent core.

In an exemplary embodiment, an adhesive is applied between the absorbent core and the liquid pervious topsheet.

In an exemplary embodiment, an acquisition and distribution layer ADL is included between the absorbent core and the liquid pervious topsheet. This serves to slow down the flow so that the liquid has adequate time to be absorbed by and evenly distributed over the absorbent core.

In an exemplary embodiment, adhesive is applied between the absorbent core and the ADL, and/or between the ADL and the liquid pervious topsheet.

In an exemplary embodiment, the attaching is such that a length of the or each attachment zone is larger than 10% of the length of the absorbent core, more preferably larger than 30%, even more preferably larger than 40%, which allows a better liquid distribution over a large area of the absorbent core.

In an exemplary embodiment, the attaching is such that the at least one attachment zone comprises at least one permanent attachment zone which remains attached when wetted, which allows the channel to distribute liquid during further liquid insults.

In an exemplary embodiment, the absorbent material comprises cellulosic fluff pulp and/or superabsorbent particles.

According to a third aspect of the invention there is provided an absorbent article comprising a liquid pervious topsheet, a liquid impervious backsheet, and an absorbent core positioned between the liquid pervious topsheet and the liquid impervious backsheet. The absorbent article has a first and second longitudinal edge and a first and second transverse edge. The absorbent core comprises a top core sheet, a back core sheet, and a layer of absorbent material arranged partially between the top core sheet and the back core sheet, wherein the top core sheet and the back core sheet do not fully wrap the absorbent material. Preferably, at least one of the top core sheet and the back core sheet comprises at least one attachment portion which is attached to the other one of the top core sheet and the back core sheet forming at least one attachment zone, and at least two edge portions covering a portion of the layer of absorbent material on either side of the at least one attachment zone. The edge portions may have a free edge but may also have one or more (or all) edges attached to the other one of top core sheet and the back core sheet.

By providing at least one of the top core sheet and the back core sheet covering only a portion of a layer of absorbent material, the at least one of the top core sheet and the back core sheet does not cover the entire top and/or bottom surface of the absorbent material, resulting in less raw material needed for the absorbent core. The at least one attachment portion forms at least one attachment zone capable of creating a channel for liquid distribution and absorption upon wetting. In this manner, at least one channel can be created with a reduced amount of material used for manufacturing the top core sheet and/or back core sheet, and as a result the manufacturing cost can be reduced while good liquid distribution and absorption capacities can be maintained. In addition, the thickness and weight of absorbent article may be reduced.

It is noted that either the top core sheet or the back core sheet may have a free edge and hence a reduced surface area compared to an absorbent core of the prior art which fully wraps the absorbent material, or both the top core sheet and the back core sheet may have a free edge. However, it is also possible to provide at least one of the top core sheet and the back core sheet with an edge portion having one edge adjacent the attachment portion and an opposite edge connected to the other one of the top core sheet and the back core sheet. This opposite edge may then be covered with absorbent material.

Preferably, seen in a top view of the absorbent core, the top core sheet has a total surface area of $S1$, the back core sheet has a total surface area of $S2$, the absorbent core has a surface area of $S0$ defined by an area covered by the absorbent material plus an area of the at least one attachment zone, wherein $S1$ is smaller than 90% of $S0$ and/or $S2$ is smaller than 90% of $S0$. $S1$ and/or $S2$ may be smaller than 80% of $S0$, preferably $S1$ and/or $S2$ may be smaller than 70% of $S0$, more preferably $S1$ and/or $S2$ may be smaller than 60% of $S0$, even more preferably $S1$ and/or $S2$ may be smaller than 50% of $S0$, most preferably $S1$ and/or $S2$ may be smaller than 40% of $S0$.

Preferably, in the at least one attachment portion substantially no absorbent material is present between the top core sheet and the back core sheet.

In an exemplary embodiment the at least one edge portion comprises a first edge portion and a second edge portion located at opposite sides of the at least one attachment portion. Both the first and the second edge portion may either have a free edge and/or a connected edge as described above.

Preferred features set out above for the absorbent article of the first aspect may also be included in the absorbent article of the third aspect.

According to a fourth aspect of the invention, there is provided a method for manufacturing an absorbent article. The method comprising:

preparing a absorbent core by providing a top core sheet and a back core sheet, and by arranging absorbent material partially between the top core sheet and the back core sheet. The top core sheet is attached to the back core sheet forming at least one attachment zone, and the arranging of absorbent material is such that at least one of the top core sheet and the back core sheet covers a portion of the absorbent material; and including the absorbent core between a liquid pervious topsheet and a liquid impervious backsheet.

By arranging the absorbent material such that at least one of the top core sheet and the back core sheet covers only a portion of the absorbent material, the at least one of the top core sheet and the back core sheet does not cover the entire top and/or bottom surface of the absorbent material, and may be provided locally where the at least one attachment portion is formed to create a channel for liquid distribution and absorption upon wetting. In this manner, at least one channel can be created with a reduced amount of material used for manufacturing the top core sheet and/or back core sheet, and as a result the manufacturing cost can be reduced while good liquid distribution and absorption capacities can be maintained. In addition, the thickness and weight of the absorbent article may be reduced.

In an exemplary embodiment, the top core sheet and the back core sheet are fed continuously in a transport direction in the form of a web top core material and a web back core material having a first width and a second width, seen in a direction perpendicular on the transport direction, respectively; wherein the absorbent material is arranged such that, seen in a direction perpendicular on the transport direction, a distance between outer limits of absorbent material is w0, wherein the distance w0 is larger than the first and/or the second width, preferably at least 10% larger, more preferably at least 20% larger, even more preferably at least 40% larger.

In an exemplary embodiment, in the at least one attachment zone substantially no absorbent material is arranged between the top core sheet and the back core sheet, preferably the at least one attachment zone is a continuous zone with substantially no absorbent material arranged between the top core sheet and the back core sheet, which allows a better liquid distribution throughout the entire channel of the absorbent core, enabling better liquid absorbance.

In an exemplary embodiment, the attaching is such that the at least one edge portion is formed, preferably a first edge portion and a second edge portion located at opposite sides of the at least one attachment portion. This provides a stable structural basis for the formation of channel after the absorbent core is wetted, and results in the formation of tubes which provide a tub shape to the absorbent core. The first and/or second edge portion may have a free or connected edge as described above for the absorbent article.

Preferred features set out above for the method of the third aspect may also be included in the method of the fourth aspect.

BRIEF DESCRIPTION OF FIGURES

The accompanying drawings are used to illustrate presently preferred non-limiting exemplary embodiments of

Figures 1A, 1B:
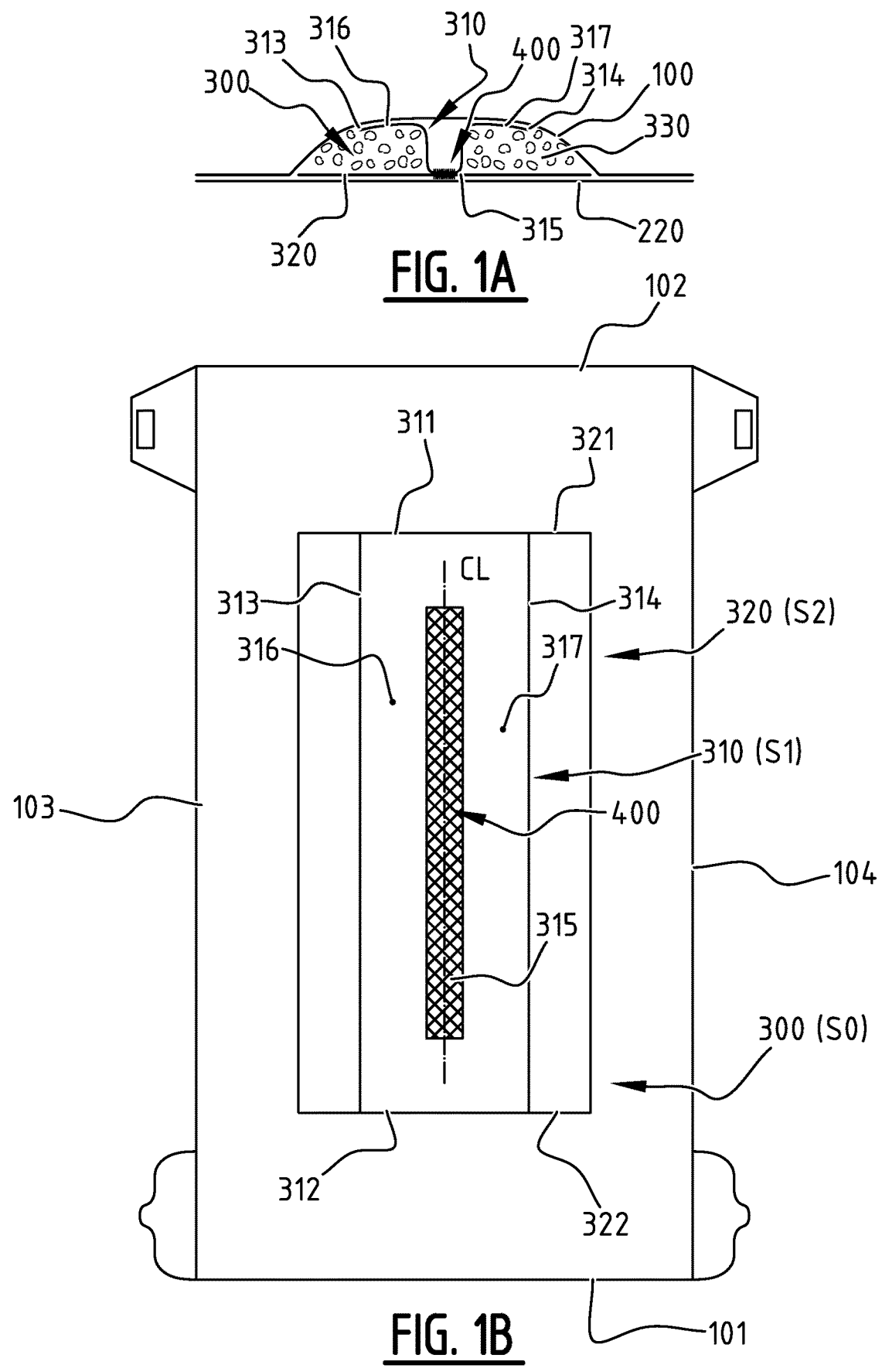
Figures 2A, 2B:
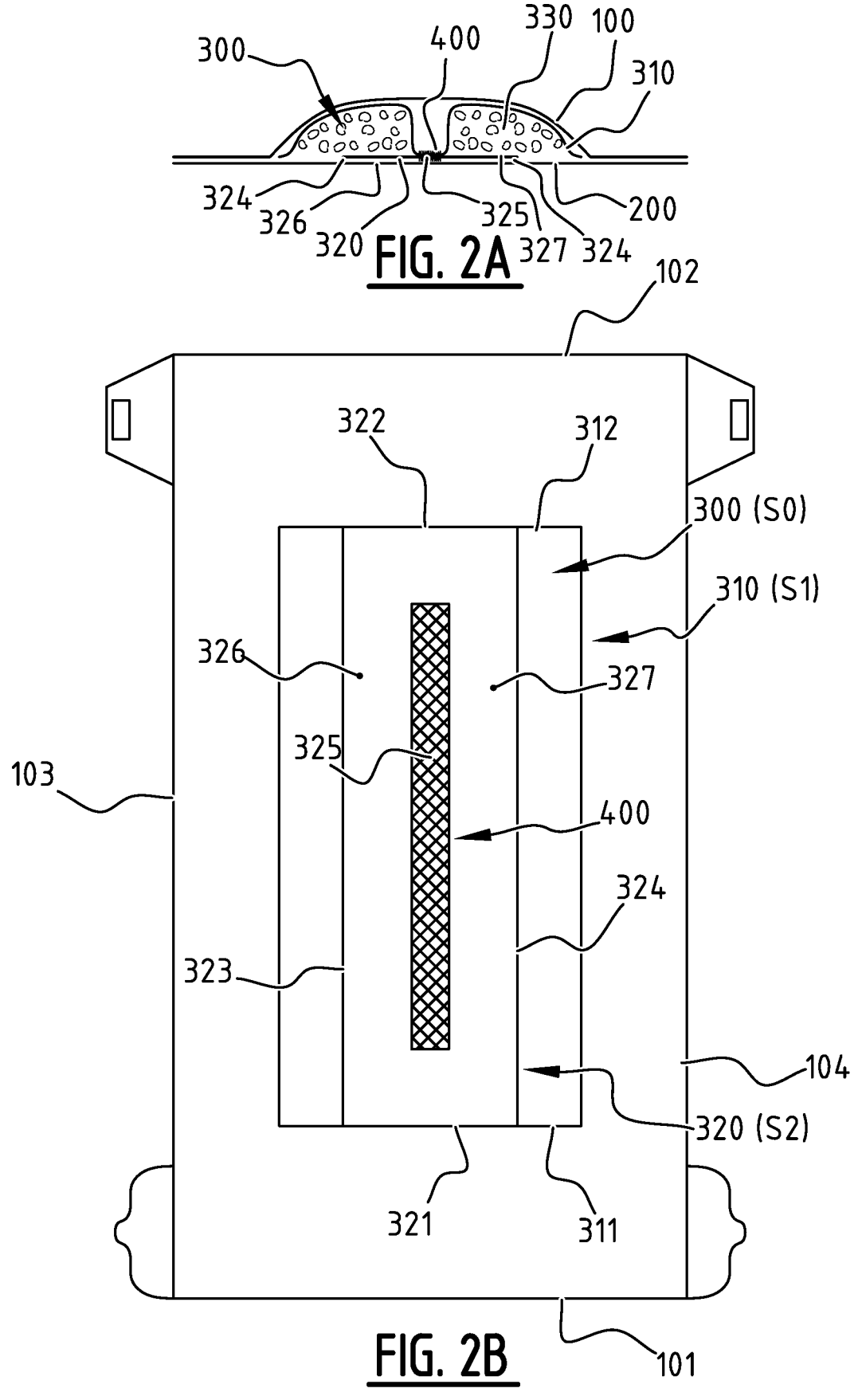
Figures 3A, 3B:
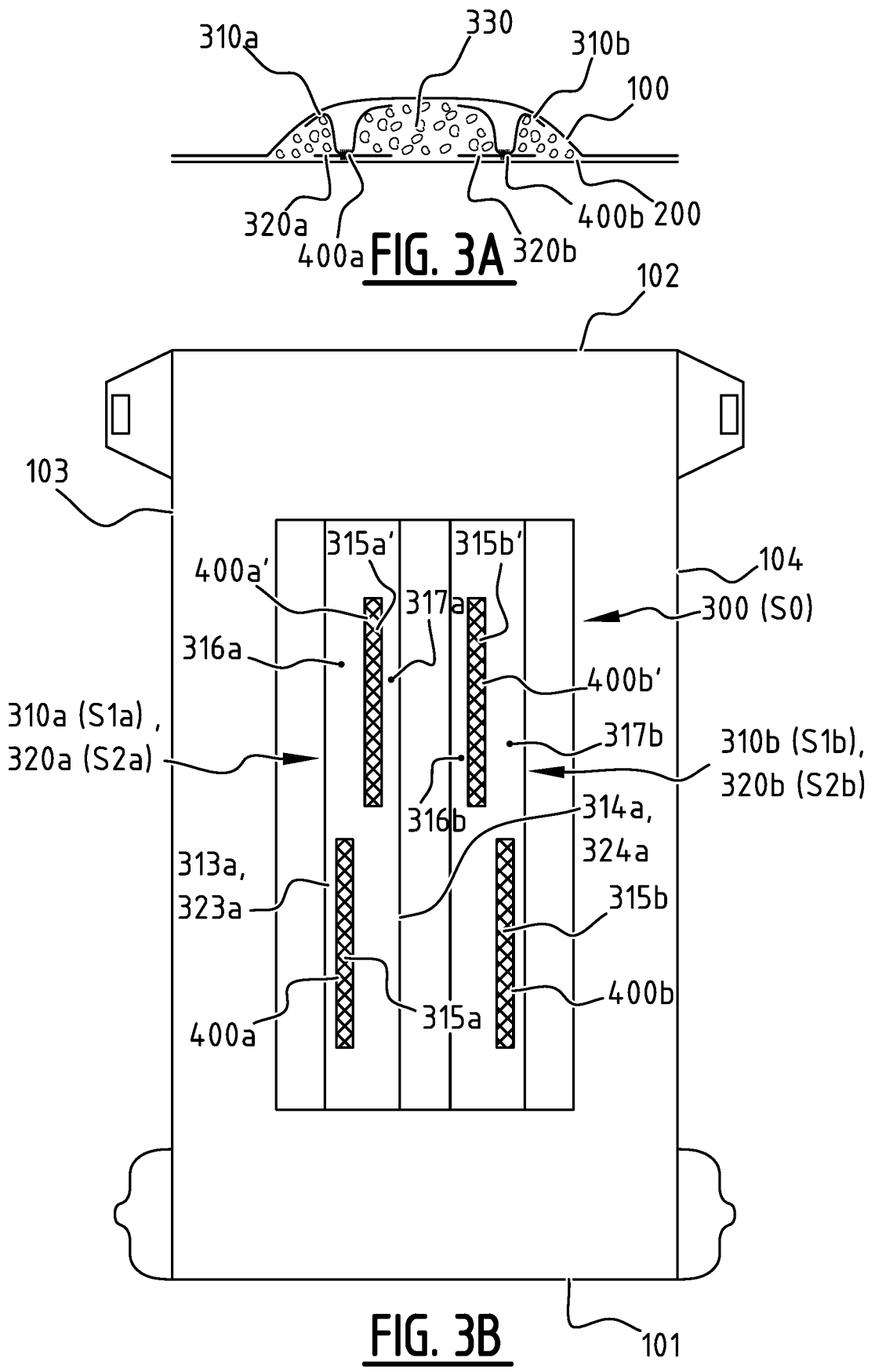
Figures 4A, 4B:
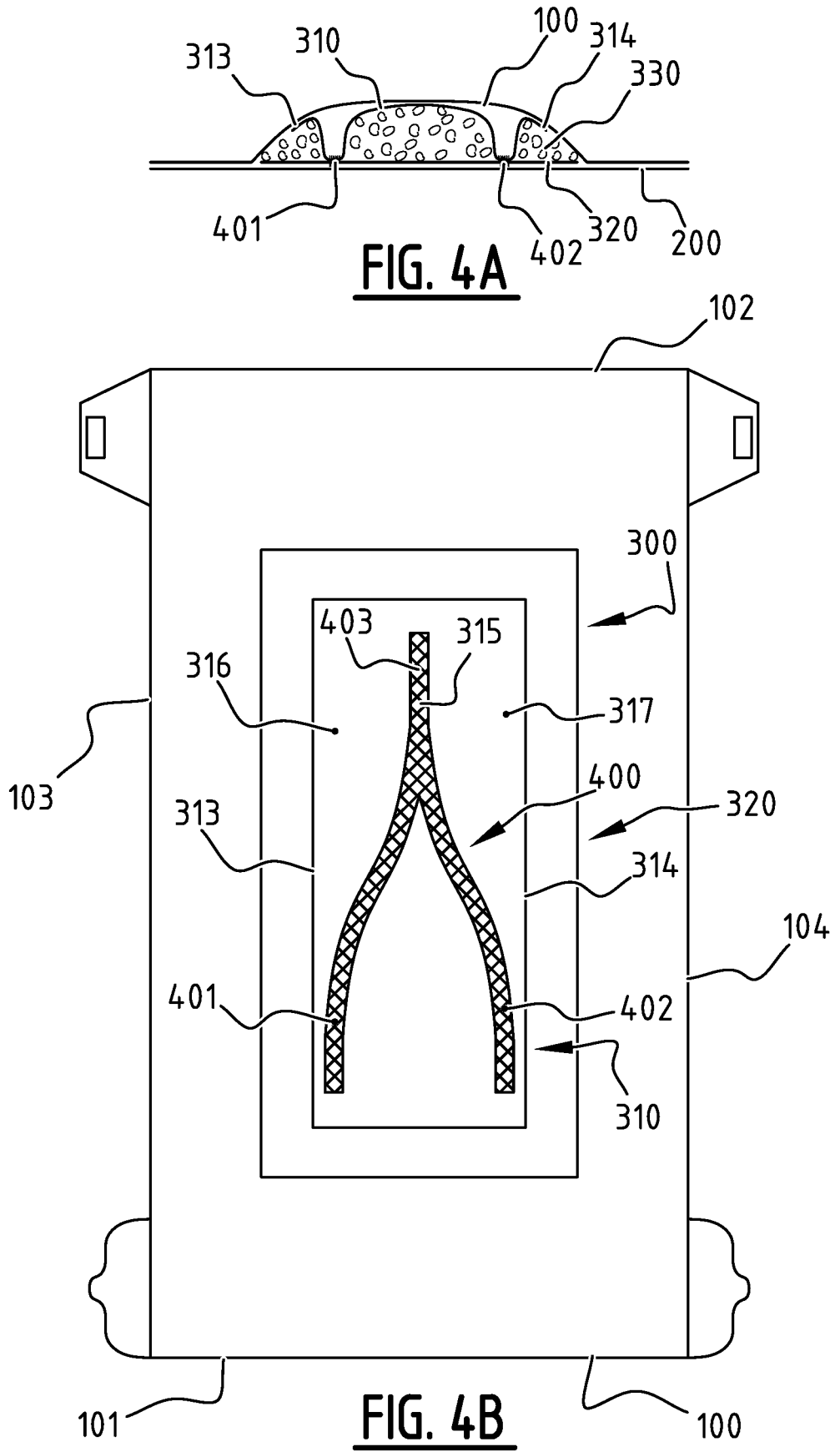
Figure 14:
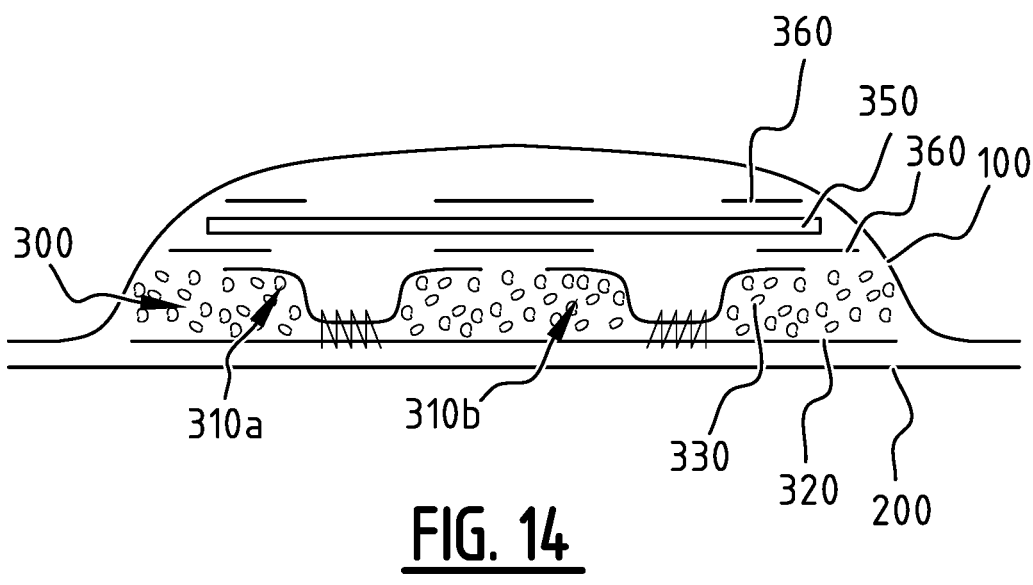
Figure 15A:
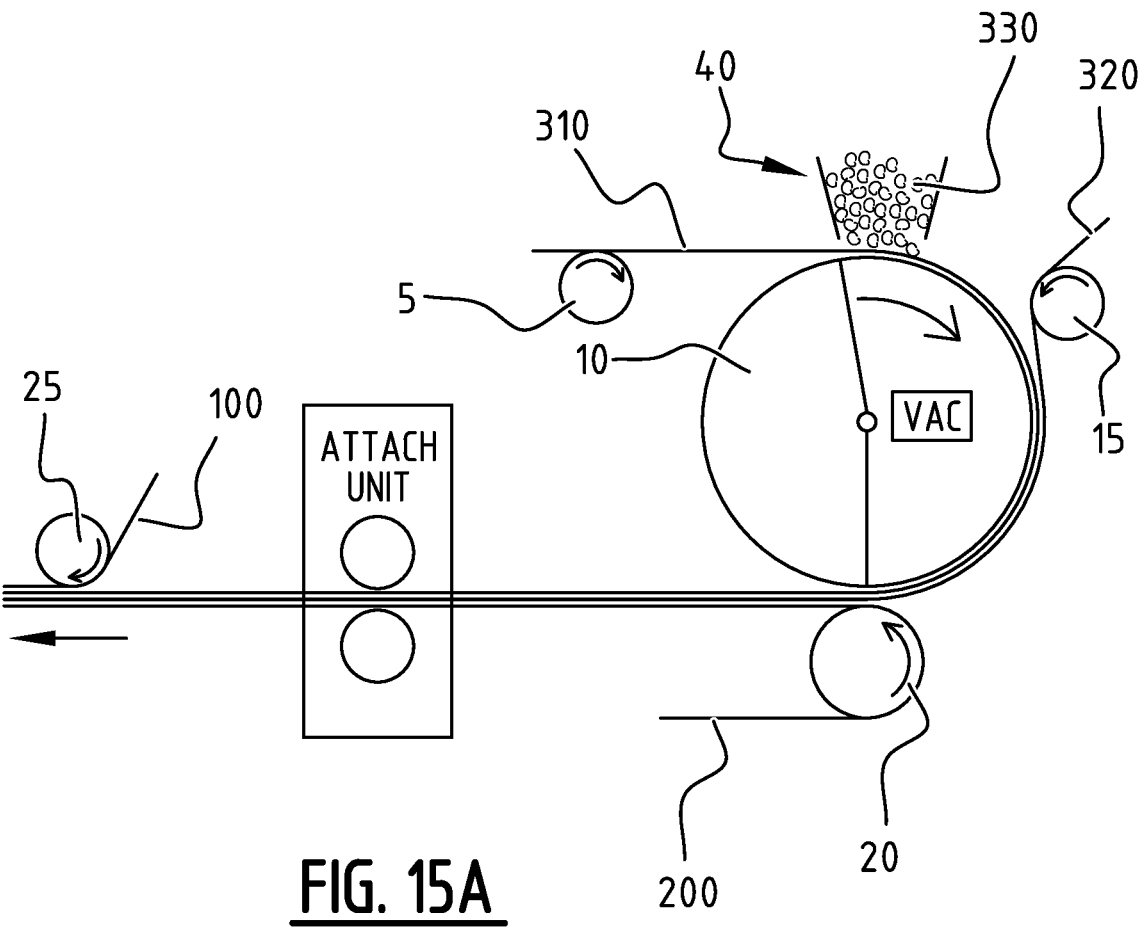
Figure 15B:
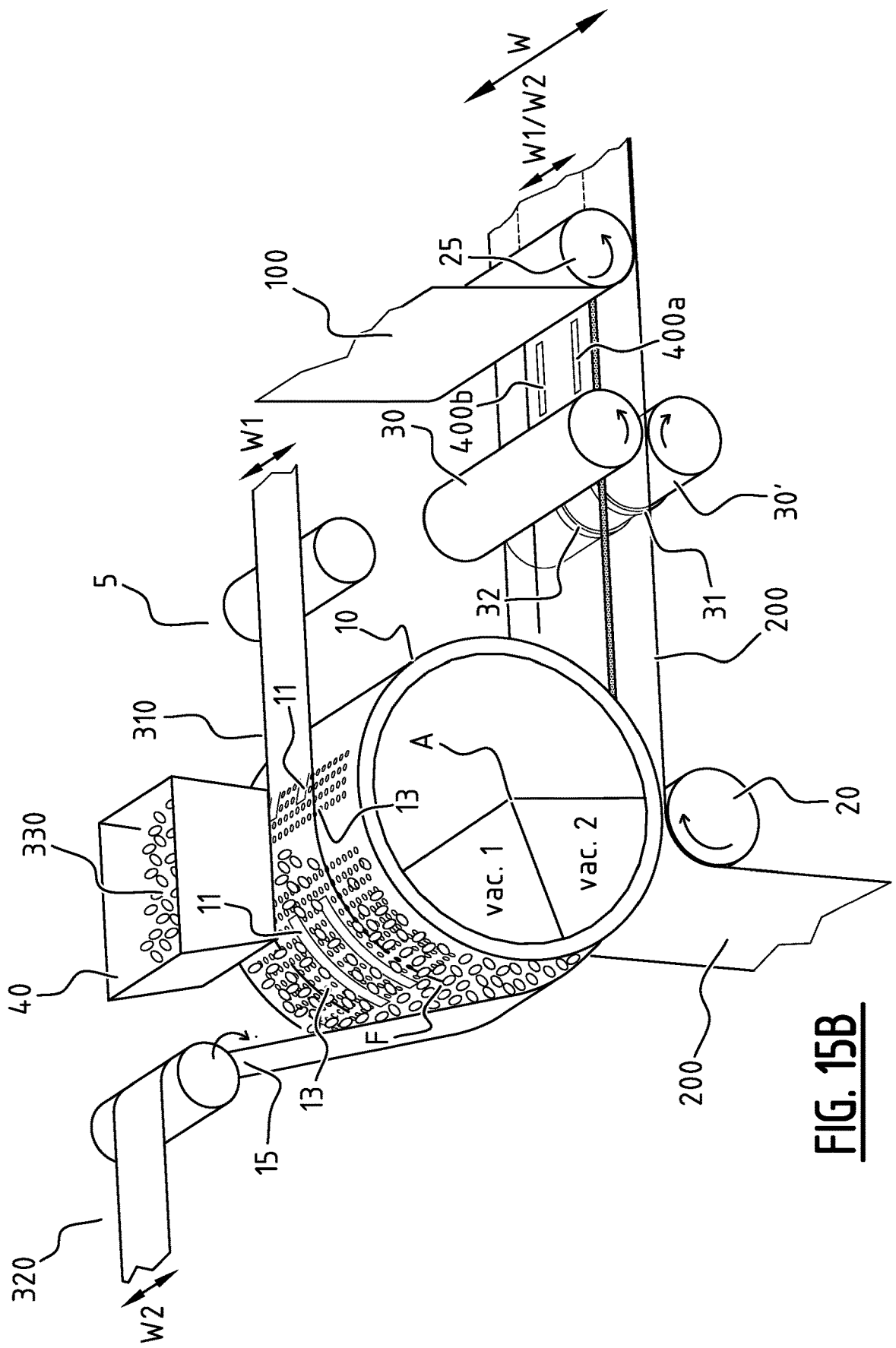
Figures 16A, 16B, 16C:
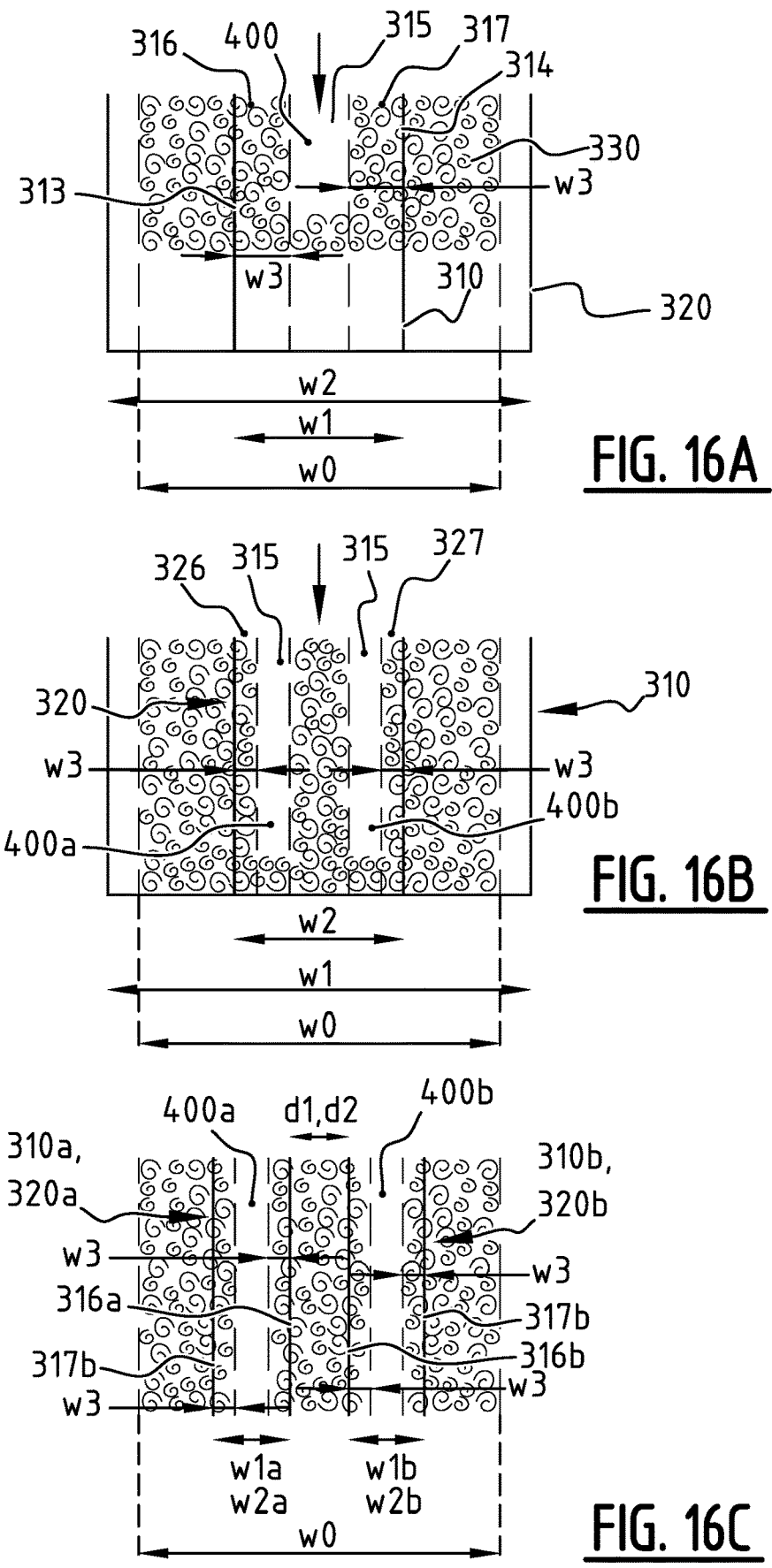

10 devices of the present invention. The above and other advantages of the features and objects of the invention will become more apparent and the invention will be better understood from the following detailed description when read in conjunction with the accompanying drawings, in which:

FIG. 1A is a schematic cross-section of an exemplary embodiment of a diaper;

FIG. 1B is a top plan view of the diaper of FIG. 1A;

FIG. 2A is a schematic cross-section of an exemplary embodiment of a diaper;

FIG. 2B is a top plan view of the diaper of FIG. 2A;

FIG. 3A is a schematic cross-section of an exemplary embodiment of a diaper;

FIG. 3B is a top plan view of the diaper of FIG. 3A;

FIG. 4A is a schematic cross-section of an exemplary embodiment of a diaper;

FIG. 4B is a top plan view of the diaper of FIG. 4A;

FIGS. 5A, 5B, 6A, 6B, 6C, 6D, 7, 8, 9A, 9B, 9C, 9D, 10, 11, 12, 13A, 13B illustrate exemplary embodiments of an absorbent core comprising zones of different layouts;

FIG. 14 a schematic cross-section of an exemplary embodiment of a diaper;

FIGS. 15A and 15B illustrate schematically an exemplary embodiment of a method and apparatus for manufacturing an absorbent article;

FIG. 16A, 16B, 16C illustrate schematically exemplary embodiments of methods for manufacturing an absorbent article.

Figures 17A, 17B:
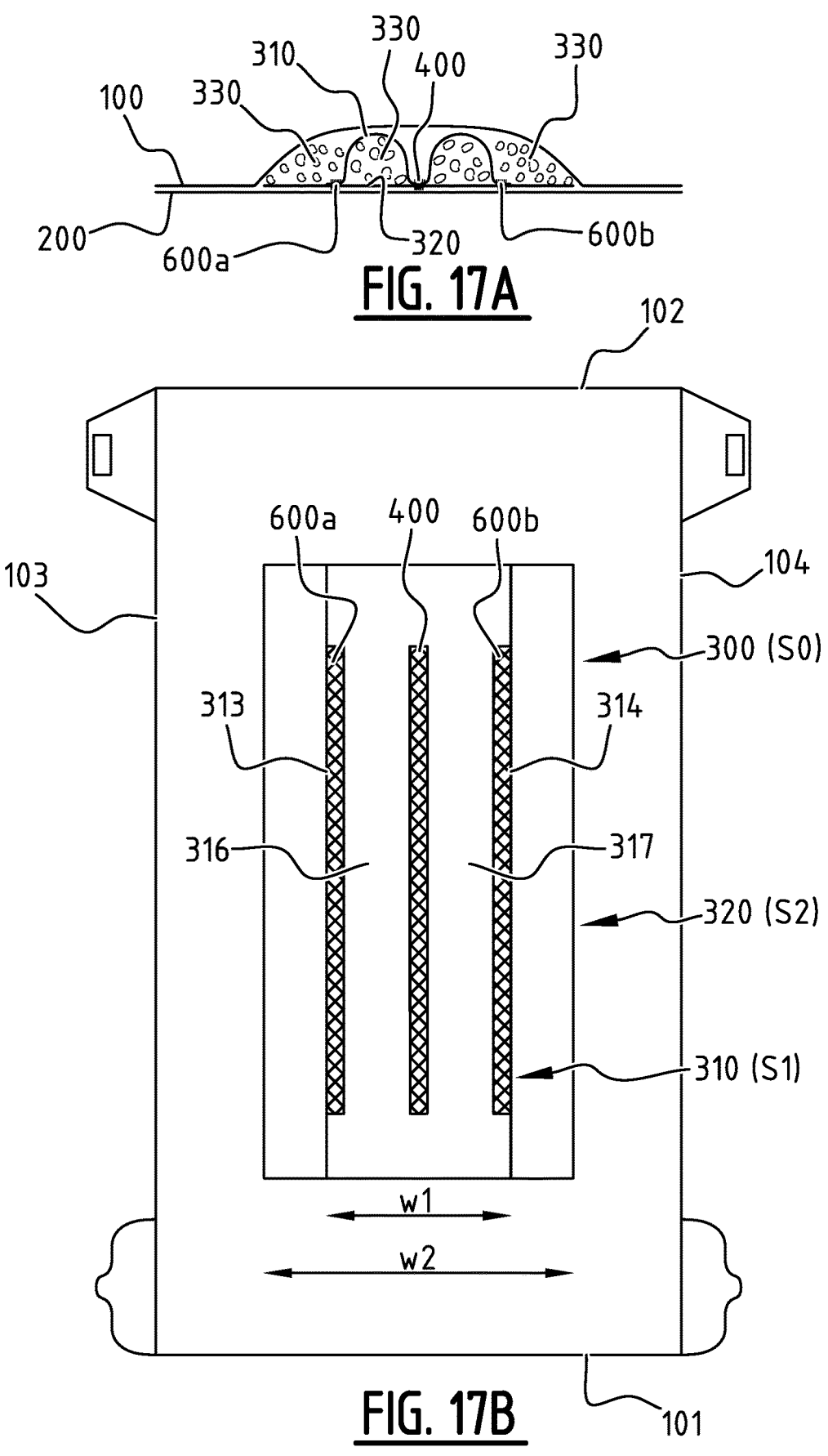

FIG. 17A is a schematic cross-section of another exemplary embodiment of a diaper;

FIG. 17B is a top plan view of the diaper of FIG. 17A;

DESCRIPTION OF EMBODIMENTS

As used herein, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to permanently absorb and/or retain bodily exudates.

"Absorbent component" as used herein refers to a structural constituent of an absorbent article, e.g., a piece of an absorbent core, such as one of multiple pieces in a multi-piece absorbent core.

"Absorbent element" as used herein refers to a part of a functional constituent of an absorbent structure, e.g., a acquisition layer, a dispersion layer, core layer or a release structure formed of a material or materials having particular liquid handling characteristics suitable for the specific function.

"Absorbent fibrous polymer material" as used herein refers to an absorbent polymer material which is in thread-like from such as fibers, filaments, and the like so as to be less flowable in the dry state than particulates.

"Absorbent insert" as used herein refers to a device adapted for insertion into an "Absorbent layer" as used herein refers to a term referring to a discrete, identifiable sheet-like or web-like element of an absorbent article which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g. bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Absorption rate" as used herein refers to the rate of absorption of liquid, i.e. the amount of liquid which is absorbed per unit of time, typically by an absorbent component, element and/or absorbent layer of the absorbent article, structure and/or core.

"Acquisition layer", "acquisition region", "acquisition surface" or "acquisition material" and the like as used herein refer to the layer overlying the absorbent core having a faster liquid uptake and/or distribution capability.

"Absorbency" is the ability of a material to take up fluids by various means including capillary, osmotic, solvent, chemical and/or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure and/or vacuum; a web of fibers produced by airlaying is herein referred to an "airlaid"; an airlaid web bonded by one or more techniques to provide fabric integrity is herein referred to an "airlaid nonwoven".

"Apparent density", "density" as used herein refers to the basis weight of the sample divided by the caliper with appropriate unit conversions incorporated therein. Apparent density used herein has the unit $g/cm^3$.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, $g/m^2$ or gsm.

"Bodily exudates", "body exudates", "bodily fluids", "body fluids", "bodily discharges", "body discharges", "fluid(s)", "liquid(s)", "fluid(s) and liquid(s) and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc), altering the chemical structure of the fibers themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garment s, baby diapers and pants and adult incontinence garments.

"Crotch region" of an absorbent article as used herein refers to about 50% of the absorbent article's total length (i.e., in the y-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them in soluble.

"Diaper", "conventional diaper", "diaper-like", "diaper-like garment" and the like as used herein are used interchangeably and refer to disposable absorbent articles, which typically include a front waist portion and a back waist portion which may be releasable connected about the hips of the wearer during use by conventional fasteners such as adhesive tape fasteners or hook and loop type fasteners. In use, the article is positioned between the legs of the wearer and the fasteners are releasable attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Dispersion layer", "dispersion region", "dispersion surface" or "dispersion material" and the like as used herein refer to the layer overlying the absorbent core having a faster liquid uptake and dispersion capability.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Drylaying" as used herein refers to a process for making a nonwoven web from dry fiber; these terms apply to the formation of carded webs, as well as to the air laying formation of random webs;

a web of fibers produced by drylaying is herein referred to as a "drylaid"; a drylaid web bonded by one or more techniques to provide fabric integrity is herein referred to a "drylaid nonwoven".

"Dry strength" as used herein refers to the strength of a joint determined in dry state conditions, immediately after drying under specified conditions or after a period of conditioning in the standard laboratory atmosphere.

"Essentially cellulose free" or "little to no cellulose fibers" as used herein refers to an absorbent article, structure, core component and/or element containing less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Essentially fluffless" or "little to no fluff pulp" as used herein refers to an absorbent article, structure, core, component and/or element containing less than 20% by weight fluff pulp, less than 10% fluff pulp, less than 5% fluff pulp, no fluff pulp, or no more than an immaterial amount of fluff pulp which do not materially affect the thinness, flexibility or absorbency thereof.

"Fabric" as used herein refers to a sheet structure made from fibers, filaments and/or yarns.

"Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width; "Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" or "Pulp fluff" as used herein refers to wood pulp specially prepared to be drylaid. The fibers can be either natural or synthetic or a combination thereof.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"High loft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to gather, bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and/or faces the wearer facing layer; conversely, the term "lower" refers to the layer of the absorbent article which is nearest to and/or faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the f low of a liquid from one absorbent element or component to another absorbent element or component by channel flow action.

"Mechanical bonding" as used herein refers to a method of bonding fibers by entangling them. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or nonrefastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Release structure", "release region", "release surface" or "release material" and the like as used herein are used interchangeably and refer to a structure in fluid communication with the absorbent core having a larger relative liquid absorption capacity and/or rate allowing it to quickly take up, temporarily hold and releasing liquids.

"Resin" as used herein refers to a solid or semisolid polymeric material.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of inter-lacing two or more sets of yarns at right angles to form a fabric; a web of fibers produced by weaving is herein referred to as a "woven".

"Web material" as used herein refers to an essentially endless material in one direction, i.e. the longitudinal exten-sion or the length, or the x-direction in Cartesian coordinates relative to the web material. Included in this term is an essentially unlimited sequence of pieces cut or otherwise separated from an essentially endless material. Often, though not necessarily, the web materials will have a thick-ness dimension (i.e. the z-direction) which is significantly smaller than the longitudinal extension (i.e. in x-direction). Typically, the width of web materials (they-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or nonwoven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or ele-ment. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The same or similar features and components are indi-cated with the same reference numerals throughout the figures.

FIGS. 1A and 1B illustrate an exemplary embodiment of an absorbent article, here a diaper. FIG. 1A shows a cross-section of the absorbent article, and FIG. 1B shows the absorbent article in its flat out, un-contracted state with the wearer side facing the viewer. The skilled person under-stands that the absorbent article may also be a pant or an adult incontinence garment or the like. The absorbent article comprising a liquid pervious topsheet 100, a liquid imper-vious backsheet 200, and an absorbent core 300 positioned between the liquid pervious topsheet 100 and the liquid impervious backsheet 200. In a possible embodiment the absorbent article may further comprise adhesive between the absorbent core 300 and the liquid pervious topsheet 100. The absorbent article has a first and second longitudinal edge 103, 104 and a first and second transverse edge 101, 102.

The absorbent core 300 comprises a top core sheet 310, a back core sheet 320, and absorbent material 330 arranged partially between the top core sheet 310 and the back core sheet 320. The top core sheet 310 comprises an attachment portion 315 which is attached to the back core sheet 320 forming an attachment zone 400, and edge portions 316, 317 covering a portion of the absorbent material 330. Each edge portion 316, 317 has a free edge 313, 314, and the free edges 313, 314 are not connected to the back core sheet 320. The first edge portion 316 and the second edge portion 317 are located at opposite sides of the attachment portion 315. In this manner the first edge portion 316 and the second edge portion 317 provide a stable structural basis for the forma-tion of a channel. When the absorbent core is wetted, the absorbent material swells such that the first edge portion 316 and the second edge portion 317 form embankments delim-iting the channel for guiding the liquid. A portion of the absorbent material 330 is not covered by the top core sheet 310. In a possible embodiment the top core sheet 310 may be attached to the liquid pervious topsheet 100, e.g. using adhesive. The attachment zone 400 extends from the crotch region CR in the direction of the first and second transverse edge 101, 102. Upon wetting of the absorbent material 330, a channel is created at said attachment zone 400. The absorbent material 330 may swell upon wetting, and the edge portions 316, 317 may prevent the absorbent material 330 from entering the attachment zone 400 and help with formation of embankments delimiting the channel upon wetting. This embodiment allows the amount of raw mate-rial for manufacturing the top core sheet 310 to be reduced, and as a result the manufacturing cost can be reduced. Meanwhile an absorbent article with good liquid distribution and absorption capacities can still be obtained.

Seen in a top view of the absorbent core, the top core sheet 310 has a total surface area of S1, the back core sheet 320 has a total surface area of S2, the absorbent core 300 has a surface area of S0 defined by an area covered by the absorbent material 330 plus an area of the attachment zone 400. S1 is smaller than 90% of S0 and/or S2 is smaller than 90% of S0, preferably S1 and/or S2 is smaller than 80% of S0, more preferably S1 and/or S2 is smaller than 70% of S0, even more preferably S1 and/or S2 is smaller than 60% of S0, even more preferably S1 and/or S2 is smaller than 50% of S0, most preferably S1 and/or S2 is smaller than 40% of S0. In the embodiment of FIGS. 1A and 1B, S1 is approxi-mately 60% of S0 while S2 is substantially the same as S0.

The attachment zone 400 has a center line CL, which is a straight line. In other embodiments, the center line CL may be a curve, or a polyline, or other shapes. The center line is a line which is at the same distance of opposite edges of the attachment zone 400, which preferably extends in a length direction of the attachment zone 400. The attachment zone 400 extends from a crotch region in the direction of the first and second transverse edge of the absorbent article 101, 102, which allows a better liquid distribution between crotch region and front/back portion of absorbent article. In other embodiments, the at least one attachment zone may extend in the direction from the first longitudinal edge 103 to the second longitudinal edge 104 of the absorbent article, which allows a better liquid distribution between left and right portions of absorbent article. However, it is also possible for the at least one attachment zone to extend under a small angle with respect to the longitudinal direction of absorbent core 300, e.g. an angle between 5 and 10°. Preferably the at least one attachment zone is arranged symmetrically with respect to a longitudinal center line of absorbent core 300. A contour of the attachment zone 400 is adjacent to the absorbent material, which may comprises cellulosic fluff pulp and/or superabsorbent particles. A length of the attachment zone 400 is larger than 10% of the length of the absorbent core 300, more preferably larger than 30%, even more preferably larger than 50%, which allows a better liquid distribution over a larger area of the absorbent core 300. The attachment zone 400 may be a permanent attachment zone which remains attached when wetted, allowing the channel to distribute liquid during consecutive liquid insults.

The top core sheet 310 and the back core sheet 320 have a substantially rectangular shape. The top core sheet 310 has a longitudinal dimension which is substantially 100% of the length of the absorbent core 300 and a transverse dimension which is about 60% of the width of the absorbent core 300, while the longitudinal and transverse dimension of the back core sheet 320 is substantially the same as the length and width of the absorbent core 300, respectively. In this embodiment, a rear and front edge of the top core sheet 310 is attached to a rear and front edge of the back core sheet 320, respectively, providing a stable and integrated structure of the absorbent core 300 while the use of material can still be reduced.

Figures 5A, 5B, 6A, 6B:
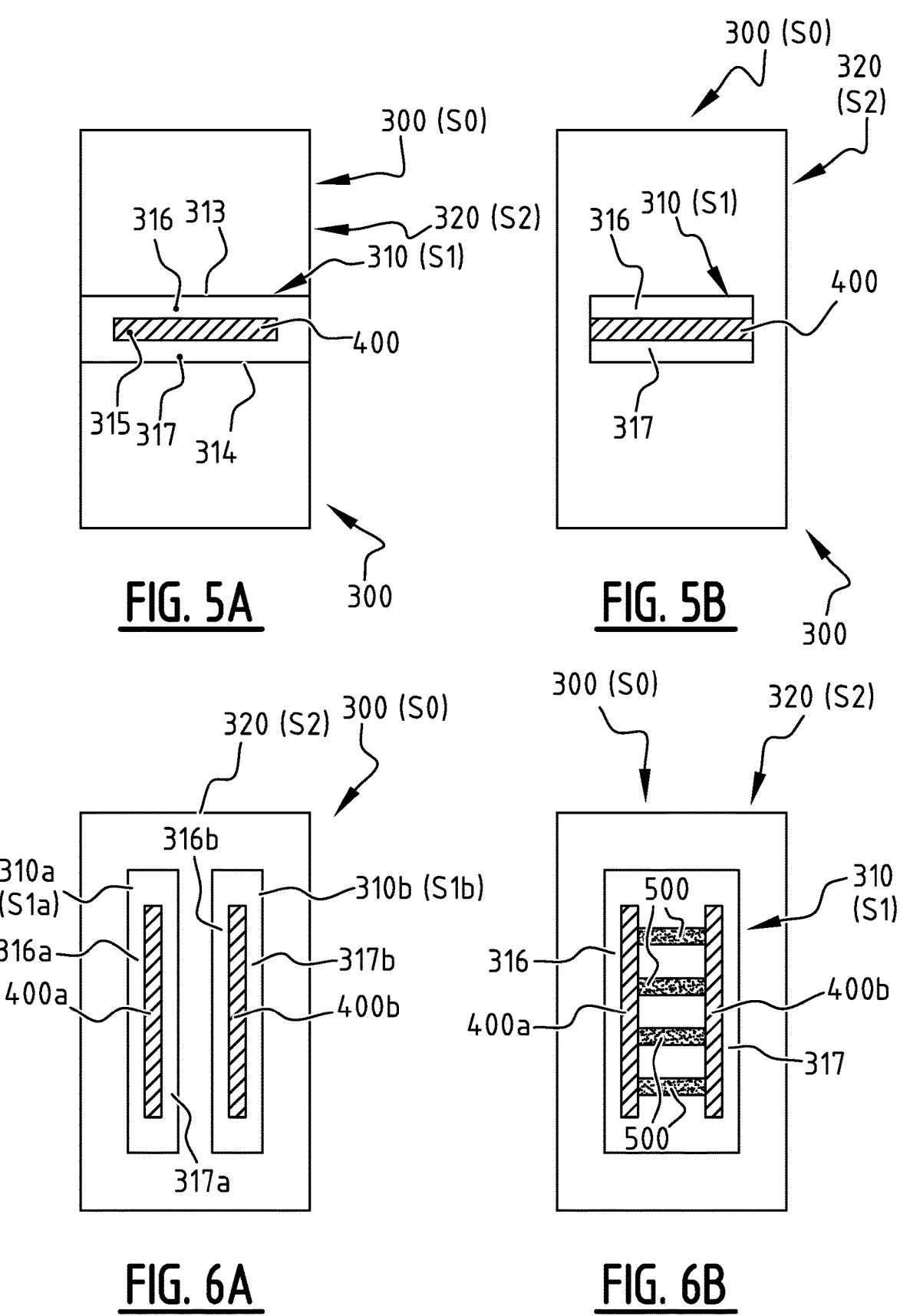

In other embodiments, e.g. the embodiment of FIG. 5A, a transverse dimension of the top core sheet 310 and/or a transverse dimension of the back core sheet 320 and the width of the absorbent core 300 may be within ±10% difference, preferably substantially the same, which allows an attachment between the top core sheet 310 and the back core sheet 320 by the longitudinal edges of the absorbent core 300.

Preferably the attachment between top core sheet 310 and back core sheet 320 may be a permanent attachment; and absorbent core 300 is configured such that, in a wetted state of absorbent core 300, the absorbent material 330 may extend partially over a bottom of the channel. Alternatively, the attachment between top core sheet 310 and back core sheet 320 may be a semi-permanent attachment configured to release after having been in contact with urine for a predetermined period of time, and the predetermined period of time is preferably smaller than 30 s.

The attachment zone 400 is provided by means of continuous attachments in the longitudinal direction of the absorbent core in FIGS. 1A and 1B. It is clear to the skilled person that in a possible embodiment the attachment zone may be provided by means of continuous attachments in the transversal direction of the absorbent core and/or discontinuous attachments in the transversal direction of the absorbent core and/or discontinuous attachments in the longitudinal direction of the absorbent core.

The channel created by the attachment zone 400 may be indicated with a color and/or with a pattern which is different from the color and/or pattern of topsheet. More in particular the area of the channel may comprise a print allowing a user to visually distinguish the at least one channel. This print may be arranged on the topsheet 100, on the top core sheet 310, on the back core sheet 320, on the backsheet 200, or on any sheet in between the topsheet 100 and the backsheet 200, as long as it is visible for a user. As the sheets may be partially transparent, the print may be arranged on a sheet in between the topsheet 100 and the backsheet 200, as long as it is visible through the topsheet 100 and/or the backsheet 200. Preferably the print is visible when looking at the topsheet 100 of the diaper.

FIGS. 2A and 2B illustrate another exemplary embodiment of an absorbent article which is similar to the embodiment of FIGS. 1A and 1B, here a diaper. The absorbent core 300 comprises a top core sheet 310, a back core sheet 320, and absorbent material 330 arranged partially between the top core sheet 310 and the back core sheet 320. The back core sheet 320 comprises an attachment portion 325 which is attached to the back core sheet 320 forming an attachment zone 400, and edge portions 326, 327 covering a portion of the absorbent material 330. Each edge portion 326, 327 has a free edge 323, 324, and the free edges 323, 324 are not connected to the top core sheet 310. The first edge portion 326 and the second edge portion 327 are located at opposite sides of the attachment portion 325. A portion of the absorbent material 330 is not covered by the back core sheet 320. Meanwhile an entire area of the absorbent material may be covered by the top core sheet 310. Thus, S2 is smaller than 60% of S0, and S1 is substantially the same as S0. This embodiment has the advantage that the amount of material used for manufacturing the back core sheet 320 can be reduced while at least one channel with good liquid distribution and absorbent capacities can still be created.

FIGS. 3A and 3B illustrate another exemplary embodiment of an absorbent article, here a diaper. The absorbent core 300 comprises a first top core sheet 310a, a second top core sheet 310b, a first back core sheet 320a, a second back core sheet 320b, and absorbent material 330 arranged partially between the first top core sheet 310a and the first back core sheet 320a, as well as between the second top core sheet 310b and the second back core sheet 320b. The first top core sheet 310a comprises two attachment portions 315a, 315a' which are attached to the first back core sheet 320a forming two attachment zones 400a, 400a', and edge portions 316a, 317a covering a portion of the absorbent material. Each edge portion 316a, 317a has a free edge 313a, 314a, and the free edges 313a, 314a are not connected to the first back core sheet 320a. Likewise, the second top core sheet 310b comprises two attachment portions 315b, 315b' which is attached to the second back core sheet 320b forming two attachment zones 400b, 400b', and at least one second edge portion 316b, 317b having at least one free edge 313b, 314b and covering a portion of the absorbent material. In this manner, multiple channels can be created with a further reduced amount of material for manufacturing both the top core sheets 310a, 310b and back core sheets 320a, 320b, as a result the liquid distribution and absorption capacities of the absorbent core is further improved with a lower manufacturing cost. In addition, the quantity of liquid that can be temporarily held in channels is further increased, and the liquid can be more evenly distributed over the entire absorbent core 300.

A distance between the first top core sheet 310a and the second top core sheet 310b is at least 5% of the width of the absorbent core 300, and/or a distance between the first back core sheet 320a and the second back core sheet 320b is at least 5% of the width of the absorbent core 300. In this manner a sufficient manufacturing cost reduction can be achieved.

Seen in a top view of the absorbent core 300, the first top core sheet 310a has a total surface area of S1a, the first back core sheet 320a has a total surface area of S2a, the second top core sheet 310b has a total surface area of S1b, the second back core sheet 320b has a total surface area of S2b, the absorbent core has a surface area of S0 defined by an area covered by the absorbent material plus an area of the attachment zones. S1a, S1b, S2a, S2b may be similar, preferably substantially the same, and S1a+S1b (and S2a+S2b) is smaller than 60% of S0.

FIGS. 4A and 4B illustrate another exemplary embodiment of an absorbent article, here a diaper. According to the exemplary embodiment of FIGS. 4A and 4B, the top core sheet 310 comprises at least one attachment portion 315 which is attached to the back core sheet 320 forming an attachment zone 400, and edge portions 316, 317 having respective free edges 313, 314 and covering a portion of the absorbent material 330. The attachment zone 400 comprises a first attachment zone 401 and a second attachment branch 402 and a third attachment branch 403. The first and second attachment branches 401, 402 extend from the crotch region in the direction of the front transverse edge 101, and are interconnected to the third attachment branch 403. The third attachment branch 403 extends from the crotch region in the direction of the rear transverse edge 102, respectively. The first attachment branch 401 and the second attachment branch 402 form together a substantially U-shaped zone. The U-shaped zone 401, 402 guides the liquid from the left and right parts of the front portion to the rear portion, or vice versa. In that manner a convenient liquid distribution channel network is created, allowing the liquid to be distributed rapidly throughout the absorbent core 300. In other embodiments the front and rear may be reversed, i.e. the branches 401, 402 may be in a rear portion of the absorbent article and the third branch 403 may be in a front portion.

FIGS. 5A-13B illustrate exemplary embodiments of an absorbent core comprising attachment zones having different layouts, as well as edge portions having different shapes. The principles about the attachment zones set out below for various embodiments may also be applied in other described embodiments. In these embodiments, the absorbent core 300 at least comprises a top core sheet 310, a back core sheet 320, and absorbent material 330 arranged partially between the top core sheet 310 and the back core sheet 320. At least one of the top core sheet 310 and the back core sheet 320 comprises at least one attachment portion which is attached to the other one of the top core sheet 310 and the back core sheet 320 forming at least one attachment zone 400, and at least one edge portion 316, 317 having at least one free edge 313, 314 and covering a portion of the absorbent material 330. Further, in alternative embodiments the top core sheet and back core sheet may be reversed, i.e. sheet 310 may be back core sheet and 320 may be a top core sheet.

In the embodiment of FIG. 5A, the attachment zone 400 extends in the direction from the first longitudinal edge to the second longitudinal edge of the absorbent article. Upon wetting of the absorbent material, one channel is created at said attachment zone 400, which allows a better liquid distribution between left and right portions of absorbent article. A transverse dimension of the top core sheet 310 and a transverse dimension of the back core sheet 320 and the width of the absorbent core 300 are within ±10% difference, preferably substantially the same. A transverse dimension of the top core sheet 310 and a transverse dimension of the back core sheet 320 and the width of the absorbent core 300 are within ±10% difference, preferably substantially the same. A longitudinal dimension of the top core sheet 310 is smaller than 40% of the longitudinal dimension of the back core sheet 320 and the length of the absorbent core 300. As a result S1 is smaller than 40% of S2 (and S0). The top core sheet 310 and the back core sheet 320 may be attached at the longitudinal edges of the absorbent core 300. The top core sheet 310 comprises an attachment portion 315 and two edge portions 316, 317 having respective free edges 313, 314 extending in a transverse direction on either side of the attachment portion 315.

The embodiment of FIG. 5B is similar to the embodiment of FIG. 5A, with the difference that the top core sheet 310 has a transverse dimension which is narrower than the width of the absorbent core 300 and the transverse dimension of the back core sheet 320.

In the embodiment of FIG. 6A, the absorbent core 300 comprises a first top core sheet 310a, a second top core sheet 310b, a back core sheet 320, and absorbent material 330 arranged partially between the first top core sheet 310a and the back core sheet 320, as well as between the second top core sheet 310b and the back core sheet 320. The first top core sheet 310a comprises an attachment portion which is attached to the back core sheet 320 forming a first attachment zone 400a. Likewise, the second top core sheet 310b comprises an attachment portion which is attached to the back core sheet 320 forming one attachment zones 400b. The first attachment zone 400a and the second attachment zone 400b may extend in parallel in the longitudinal direction of the absorbent core 300, from the crotch region of the absorbent core to the front and the rear transverse edge of the absorbent core. Seen in a top view of the absorbent core 300, the first top core sheet 310a has a total surface area of S1a, the second top core sheet 310b has a total surface area of S1b, the back core sheet 320 has a total surface area of S2, and the absorbent core has a surface area of S0. S1a and S1b are substantially the same, and S2 and S0 are substantially the same, and S1a+S1b is smaller than 40% of S0. The distance between the first top core sheet 310a and the second top core sheet 310b is at least 5% of the width of the absorbent core 300.

In the embodiment of FIG. 6B, the at least one attachment portion comprises a first attachment zone 400a and a second attachment zone 400b. Both of the first attachment zone 400a and the second attachment zone 400b may have a shape of a substantially straight line. The first and second attachment zones 400a, 400b extend in parallel from the crotch region in the direction of the front and the rear transverse edge of the absorbent article. The first and second attachment zones 400a, 400b may be connected through at least one semi-permanent attachment zone 500, preferably extending in a substantially transverse direction. In this manner liquid can flow in a transverse direction through the absorbent material of the absorbent core. The back core sheet 320 and the absorbent core 300 have substantially the same longitudinal dimension and transverse dimension. The longitudinal and transverse dimension of the top core sheet 310 is smaller than the longitudinal and transverse dimension of the back core sheet 320 (and the absorbent core 300). S1 is smaller than 40% of S2 (and S0).

FIG. 6C shows a similar embodiment as the embodiment of FIG. 3B, with the difference that only one attachment zone 400*a* is formed between the first top core sheet 310*a* and the first back core sheet 320*a*, and only one attachment zone 400*b* is formed between the second top core sheet 310*b* and the second back core sheet 320*b*. The attachment zones 400*a*, 400*b* extend in parallel in the longitudinal direction of the absorbent core 300, from the crotch region of the absorbent core to the front and the rear transverse edges of the absorbent core. The first top core sheet 310*a* comprises edge portions 316*a*, 317*a* covering a portion of the absorbent material. Likewise, the second top core sheet 310*b* comprises second edge portions 316*b*, 317*b* covering a portion of the absorbent material. The first back core sheet 320*a* comprises edge portions 326*a*, 327*a* covering a portion of the absorbent material. Likewise, the second back core sheet 320*b* comprises second edge portions 326*b*, 327*b* covering a portion of the absorbent material.

FIG. 6D shows a similar embodiment as the embodiment of FIG. 6C. In this embodiment, at least one semi-permanent attachment zone 500*a* is further formed between the first top core sheet 310*a* and the first back core sheet 320*a*. Likewise, at least one semi-permanent attachment zone 500*b* is further formed between the second top core sheet 310*a* and the second back core sheet 320*a*. The at least one semi-permanent attachment zones 500*a*, 500*b* extend in a substantially transverse direction of the absorbent core 300, and cross the first attachment zone 400*a* and the second attachment zone 400*b*, e.g. perpendicularly. In this manner liquid can flow in a transverse direction through the absorbent material of the absorbent core. The first top core sheet 310*a* comprises edge portions 316*a*, 317*a* covering a portion of the absorbent material. Likewise, the second top core sheet 310*b* comprises second edge portions 316*b*, 317*b* covering a portion of the absorbent material. The first back core sheet 320*a* comprises edge portions 326*a*, 327*a* covering a portion of the absorbent material. Likewise, the second back core sheet 320*b* comprises second edge portions 326*b*, 327*b* covering a portion of the absorbent material. It is noted that the edge portions 316*a*, 317*a*, 316*b*, 317*b*, 326*a*, 327*a*, 326*b*, 327*b* have respective free edges in between the semi-permanent attachment zones 500*a*, 500*b*.

In the embodiment of FIG. 7, the absorbent core 300 comprises a first top core sheet 310*a*, a second top core sheet 310*b*, a back core sheet 320, and absorbent material 330 arranged partially between the first top core sheet 310*a* and the back core sheet 320, as well as between the second top core sheet 310*b* and the back core sheet 320. The first top core sheet 310*a* comprises an attachment portion which is attached to the back core sheet 320 forming a first attachment zone 400*a*. Likewise, the second top core sheet 310*b* comprises an attachment portion which is attached to the back core sheet 320 forming one attachment zones 400*b*. The first top core sheet 310*a* comprises edge portions 316*a*, 317*a* covering a portion of the absorbent material. Likewise, the second top core sheet 310*b* comprises second edge portions 316*b*, 317*b* covering a portion of the absorbent material. The first attachment zone 400*a* and the second attachment zone 400*b* diverge from the crotch region in the direction of a front and rear transverse edge of absorbent core. The center line of the first attachment zone 400*a* and the second attachment zone 400*b* may have a curved shape. The first top core sheet 310*a* and the back core sheet 320 may further be attached at the transverse edges of the absorbent core 300, and likewise for the second top core sheet 310*b* and the back core sheet 320. Seen in a top view of the absorbent core 300, the first top core sheet 310*a* has a total surface area of S1*a*, the second top core sheet 310*b* has a total surface area of S1*b*, the back core sheet 320 has a total surface area of S2, and the absorbent core has a surface area of S0. S1*a* and S1*b* are substantially the same, and S2 and S0 are substantially the same, and S1*a*+S1*b* is smaller than 60% of S0. The distance between the first top core sheet 310*a* and the second top core sheet 310*b* is at least 5% of the width of the absorbent core 300.

In the embodiment of FIG. 8, a longitudinal dimension of the top core sheet 310 and a longitudinal dimension of the back core sheet 320 and the length of the absorbent core 300 are within ±10% difference, preferably substantially the same. A transverse dimension of the top core sheet 310 and a transverse dimension of the back core sheet 320 are substantially the same, and are smaller than 80% of the transverse dimension of the absorbent core 300. As a result, S1 and S2 are substantially the same, and S1 and S2 are smaller than 80% of S0. The top core sheet 310 and the back core sheet 320 may further be attached at the transverse edges of the absorbent core 300. The at least one attachment portion comprises an attachment zone 400, which extends from the crotch region in the direction of the front and the rear transverse edge, and has a shape of substantially straight line. Semi-permanent attachment zones 500*a*, 500*b* are formed between top core sheet 310 and back core sheet 320. As is illustrated, the front ends and rear ends and mid-portions of the semi-permanent attachment zones 500*a*, 500*b* and the attachment zone 400 may be connected. The semi-permanent attachment zones 500*a*, 500*b* together form a substantial "8" shape, and the attachment zone 400 is located on the center line of the "8" shape. In this manner liquid can flow in a both transverse and longitudinal direction through the absorbent material of the absorbent core, and liquid may be better distributed over the absorbent core.

Figures 9A, 9B, 9C, 9D:
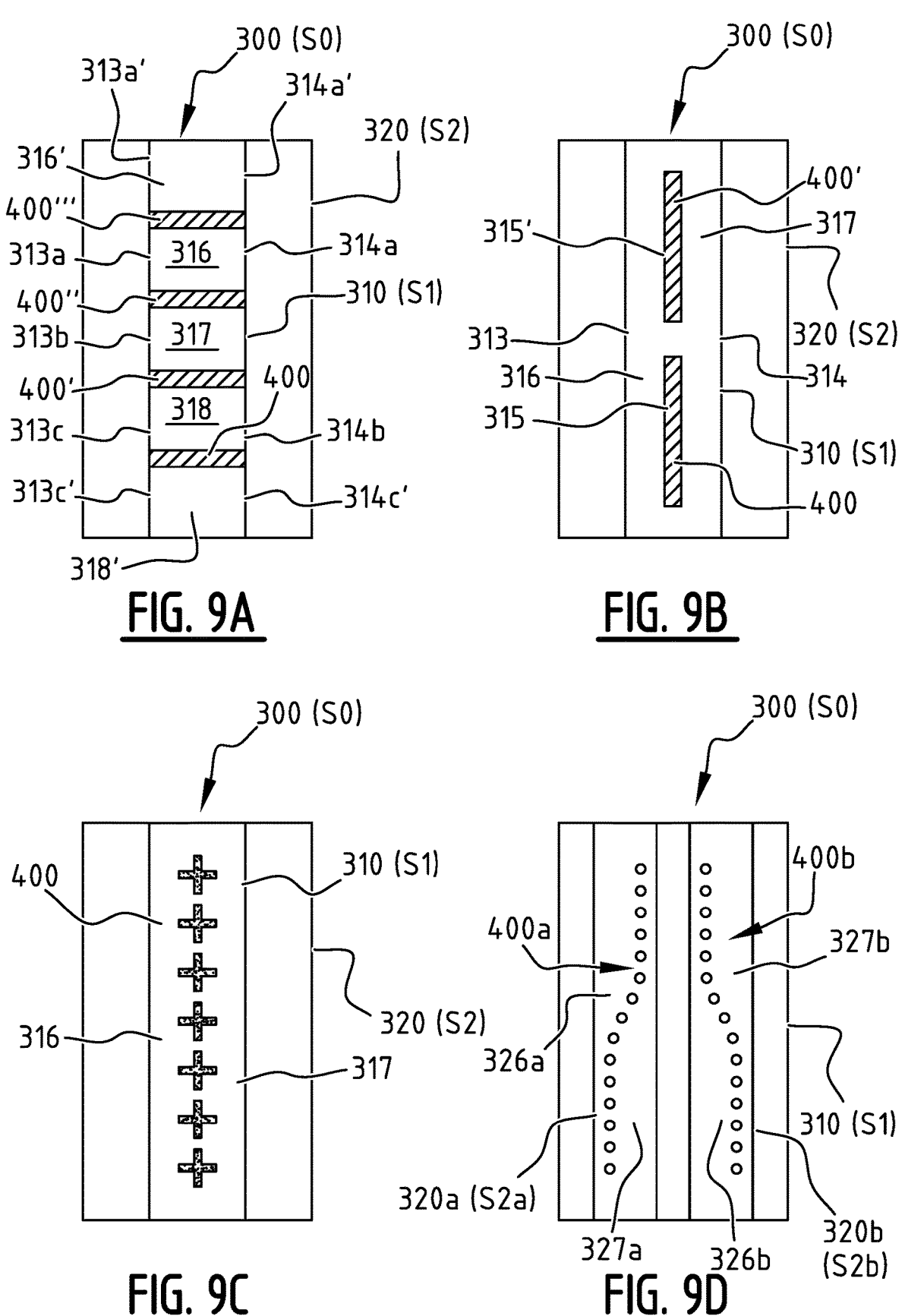

In the embodiments of FIG. 9A, 9B, 9C, a longitudinal dimension of the top core sheet 310 and a longitudinal dimension of the back core sheet 320 and the length of the absorbent core 300 are within ±10% difference, preferably substantially the same. A transverse dimension of the back core sheet 320 and a transverse dimension of the absorbent core 300 are substantially the same, and a transverse dimension of the top core sheet 310 is smaller than 50% of the transverse dimension of the absorbent core 300 and the transverse dimension of the back core sheet 320. As a result, S0 and S2 are substantially the same, and S1 is smaller than 50% of S0 and S2. The top core sheet 310 and the back core sheet 320 may further be attached at the transverse edges of the absorbent core 300.

In the embodiment of FIG. 9A, the at least one attachment portion comprises a plurality of attachment zones 400, 400', 400", 400''', which extend in a transverse direction from the left portion to the right portion of the absorbent core. The length of the plurality of attachment zones 400, 400', 400", 400''' in the transverse direction may be substantially the same as the transverse dimension of the top core sheet 310. The distance between each of the plurality of attachment zones 400, 400', 400", 400''' is at least 5% of the longitudinal dimension of the absorbent core 300, and may be equally divided. At either sides of the attachment zones 400, 400', 400", 400''' edge portions 316, 316', 317, 318, 318' are formed. Each edge portion 316, 316', 317, 318, 318' has opposite free edges 313*a*, 314*a*; 313*a'*, 314*a'*; 313*b*, 314*b*; 313*c*, 314*c*; 313*c'*, 314*c'*.

In the embodiment of FIG. 9B, the at least one attachment portion comprises a plurality of attachment zones, which comprises a first attachment zone 400 and a second attachment zone 400'. The first attachment zone 400 extends from the crotch portion of the absorbent core 300 to one of the front and rear transverse edge of the absorbent core 300, and the second attachment zone 400' extends from the crotch portion of the absorbent core to the other one of the rear and front transverse edge of the absorbent core.

In the embodiment of FIG. 9C, the at least one attachment portion comprises a plurality of attachment zones 400, and each of the attachment zones may have a shape of cross. The plurality of attachment zones 400 may be positioned in a row which extends in a longitudinal direction of the absorbent core.

In the embodiment of FIG. 9D, the absorbent core 300 comprises a first back core sheet 320a, a second back core sheet 320b, a top core sheet 310, and absorbent material 330 arranged partially between the first back core sheet 320a and the top core sheet 310, as well as between the second back core sheet 320b and the top core sheet 310. The first back core sheet 320a comprises an attachment portion which is attached to the top core sheet 310 forming a first attachment zone 400a. Likewise, the second back core sheet 320b comprises one attachment portion which is attached to the top core sheet 310 forming a second attachment zones 400b. The first attachment zone 400a and the second attachment zone 400b comprises a plurality of discrete attachments such as dots which have preferably substantially no absorbent material between the top core sheet 310 and the first back core sheet 320a, and between the top core sheet 310 and the second back core sheet 320b. Meanwhile absorbent material is present in an area in-between said plurality of mini attachment zones, between the top core sheet 310 and the first back core sheet 320a, and/or between the top core sheet 310 and the second back core sheet 320b. The first attachment zone 400a and/or the second attachment zone 400b may be formed by discontinuous attachments arranged according to a pattern extending in the longitudinal direction of the absorbent core 300.

Figures 10, 11, 12, 13A:
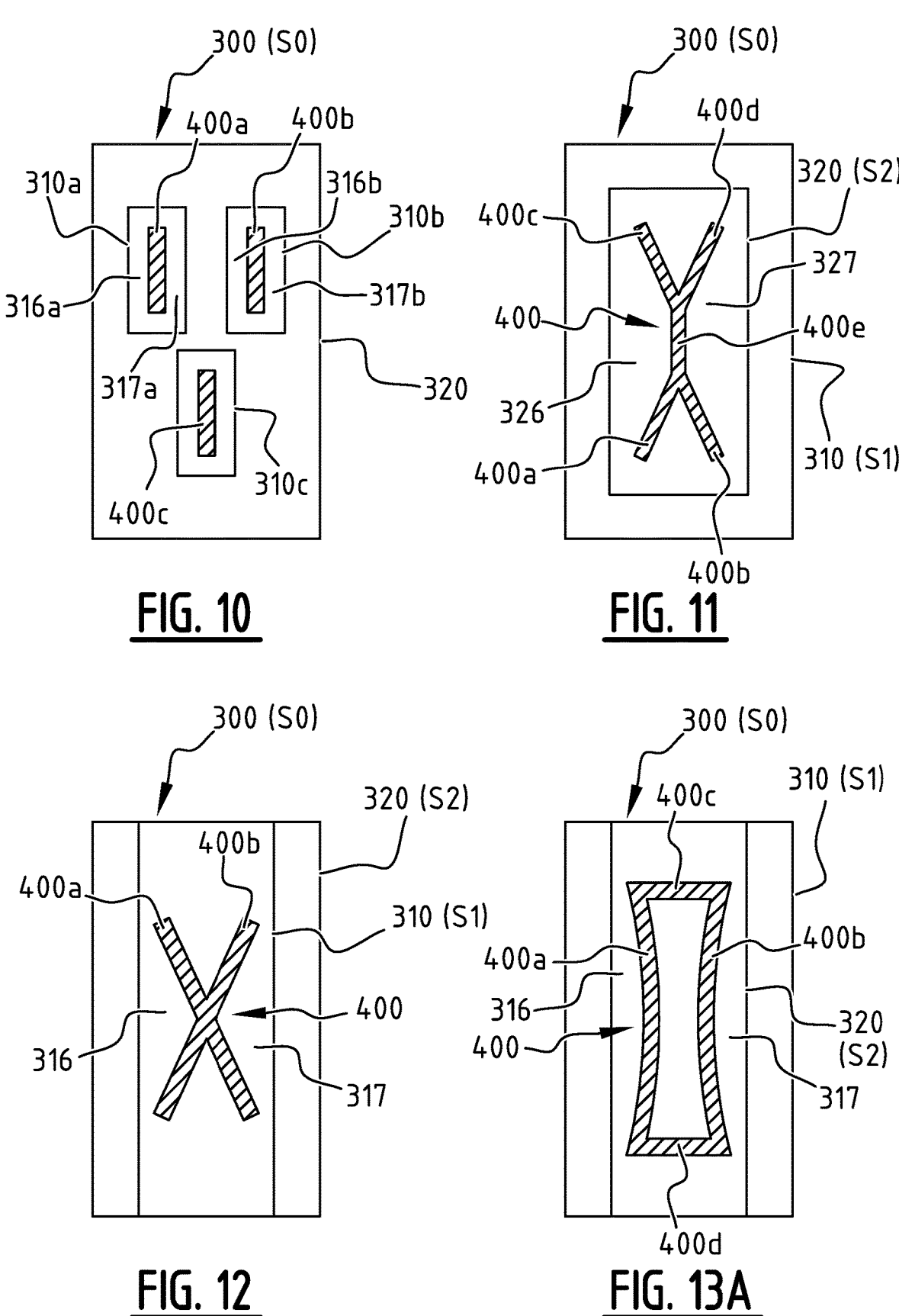

FIG. 10 shows a similar embodiment as the embodiment of FIG. 6A, with the difference that a third attachment zone 400c is further formed. The first attachment zone 400a and the second attachment zone 400b may extend in parallel in the longitudinal direction of the absorbent core 300, from the crotch region of the absorbent core 300 to the front (or the rear) transverse edge of the absorbent core. And the third attachment zone 400c may extend in the longitudinal direction of the absorbent core, from the crotch region of the absorbent core to the rear (or the front) transverse edge of the absorbent core.

In the embodiments of FIGS. 6A, 6C, 6D, 7, 9D, 10, the absorbent core 300 further comprises a second top core sheet 310b and/or a second back core sheet 320b, and at least one second attachment zone is further formed. It is possible that the absorbent article further comprising a second top core sheet 310b and a second back core sheet 320b (e.g. FIGS. 6C, 6D). The second top core sheet 310b comprises at least one second attachment portion which is attached to the second back core sheet 320b forming at least one second attachment zone 400b, and at least one second edge portion 316b, 317b having at least one free edge and covering a portion of the absorbent material. It is also possible that the absorbent article further comprising a second top core sheet 310b comprising at least one second attachment portion which is attached to the back core sheet 320 forming at least one second attachment zone 400b, and at least one second edge portion 316b, 317b having at least one free edge and covering a portion of the absorbent material (e.g. FIGS. 6A, 7, 10). It is also possible that the absorbent article further comprises a second back core sheet 320b, said second back core sheet comprising at least one second attachment portion which is attached to the top core sheet 310 forming at least one second attachment zone 400b, and at least one second edge portion 326b, 327b having at least one free edge and covering a portion of the absorbent material (e.g. FIG. 9D). A distance between the top core sheet and the second top core sheet is at least 5% of the width of the absorbent core, and/or a distance between the back core sheet and the second back core sheet is at least 5% of the width of the absorbent core.

In the embodiment of FIG. 11, the back core sheet 320 and the absorbent core 300 have substantially the same longitudinal dimension and transverse dimension. The longitudinal and transverse dimension of the back core sheet 320 is smaller than the longitudinal and transverse dimension of the back core sheet 310 (and the absorbent core 300). S2 may be smaller than 60% of S1 (and S0). The at least one attachment portion comprises a first attachment zone 400a, a second attachment zone 400b, a third attachment zone 400c and a fourth attachment zone 400d, and a central attachment zone 400e in the crotch region. The first and second attachment zones 400a, 400b diverge from the central attachment zone 400e in the direction of a rear (or front) transverse edge of absorbent core. The third and fourth attachment zone 400c, 400d diverge from the central attachment zone 400e in the crotch region in the direction of a front (or rear) transverse edge of absorbent core. The first attachment zone 400a and the second attachment zone 400b form together a substantially V-shaped zone. Similarly, the third attachment zone 400c and the fourth attachment zone 400d form together a substantially V-shaped zone. The V-shaped zones guide the liquid from left and right parts of the front and/or the rear portion. The V-shaped zones at the front and rear portion of the absorbent core are connected by a central longitudinal attachment zone 400e, and a convenient liquid distribution channel network is created allowing the liquid to be distributed rapidly throughout the absorbent core 300.

In the embodiment of FIG. 12, a longitudinal dimension of the top core sheet 310 and a longitudinal dimension of the back core sheet 320 and the length of the absorbent core 300 are within ±10% difference, preferably substantially the same. A transverse dimension of the back core sheet 320 and a transverse dimension of the absorbent core 300 are substantially the same, and a transverse dimension of the top core sheet 310 is smaller than 70% of the transverse dimension of the absorbent core 300 and the transverse dimension of the back core sheet 320. As a result, S0 and S2 are substantially the same, and S1 is smaller than 70% of S0 and S2. The top core sheet 310 and the back core sheet 320 may further be attached at the transverse edges of the absorbent core 300. The at least one attachment portion comprises at least one attachment zone 400, which comprises a first attachment zone 400a and a second attachment zone 400b. The first attachment zone 400a crosses the second attachment zone 400b at a crossing point. The first and second attachment zones 400a, 400b together form a substantially X-shaped zone. Preferably the crossing point is on a longitudinal center line of the absorbent core 300 extending between the transverse edges. Preferably the crossing point is in the crotch portion of the absorbent core 300.

Figure 13B:
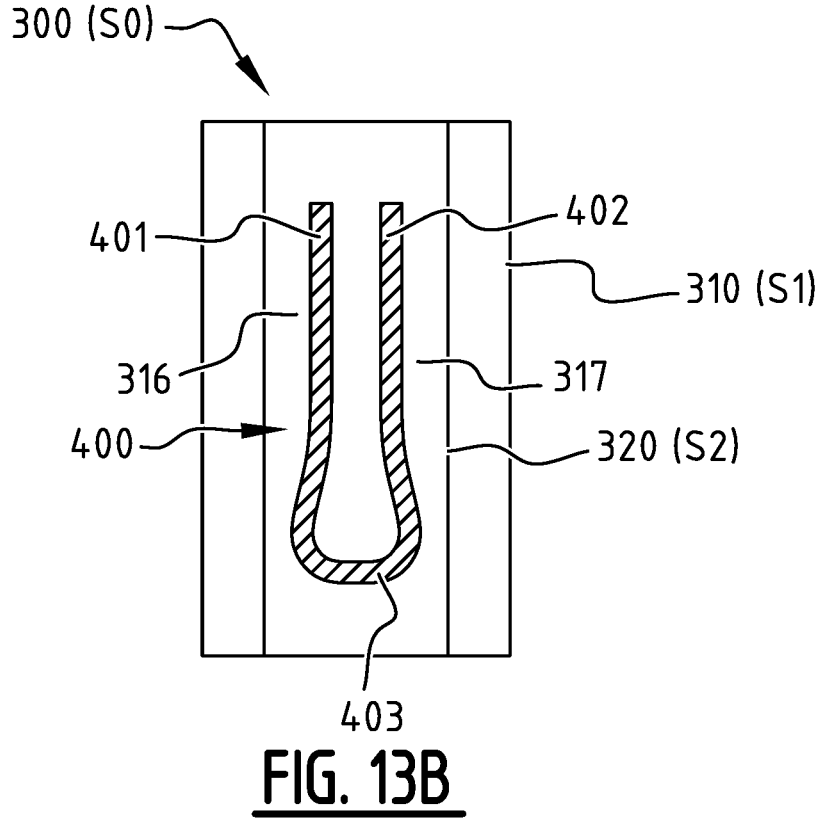

In the embodiment of FIGS. 13A and 13B, a longitudinal dimension of the top core sheet 310 and a longitudinal dimension of the back core sheet 320 and the length of the absorbent core 300 are within ±10% difference, preferably substantially the same. A transverse dimension of the top core sheet 310 and a transverse dimension of the absorbent core 300 are substantially the same, and a transverse dimension of the back core sheet 320 is smaller than 70% of the transverse dimension of the absorbent core 300 and the transverse dimension of the top core sheet 310. As a result, S0 and S1 are substantially the same, and S2 is smaller than 70% of S0 and S1. The top core sheet 310 and the back core sheet 320 may further be attached at the transverse edges of the absorbent core 300.

In the embodiment of FIG. 13A, the at least one attachment portion comprises an attachment zone 400, which comprises a first attachment zone 400_a_ and a second attachment zone 400_b_ and a third attachment zone 400_c_ and a fourth attachment zone 400_d_. The first attachment zone 400_a_ and the second attachment zone 400_b_ may extend in parallel in a longitudinal direction of the absorbent core, and the third attachment zone 400_c_ and the fourth attachment zone 400_d_ may extend in parallel in a transverse direction of the absorbent core. The front (or rear) ends of the first attachment zone 400_a_ and the second attachment zone 400_b_ may be connected by the third attachment zone 400_c_, preferably by the left and right ends of the third attachment zone 400_c_, respectively. The rear (or front) ends of the first attachment zone 400_a_ and the second attachment zone 400_b_ may be connected by the fourth attachment zone 400_d_, preferably by the left and right ends of the fourth attachment zone 400_d_, respectively. The first, second, third and fourth attachment zones 400_a_, 400_b_, 400_c_, 400_d_, together form an enclosed region with a substantially rectangular shape. Edge portions 316, 317 with free edges extend on either side of the attachment zones 400_a_, 400_b_.

In the embodiment of FIG. 13B, the at least one attachment portion comprises an attachment zone 400 which comprises a first attachment zone 401 and a second attachment zone 402, which are interconnected by a third attachment zone 403 in a front or rear portion of the absorbent core 300. In that manner any leakage via the front or rear portion can be reduced or avoided. In the embodiment of FIG. 13B the first attachment zone 401, the second attachment zone 402 and the third attachment zone 403 form together a substantially U-shaped zone. This substantially U-shaped zone comprises a first elongate attachment zone 401 (indicated as a solid fill area), a second elongate attachment zone 402 (indicated as a solid fill area), and a third attachment zone 403 (indicated as a hatched area). The first and second elongate attachment zone 401, 402 extend next to each other from the crotch region in the direction of the front transverse edge and in the direction of the rear transverse edge. The third attachment zone 403 connects said first elongate attachment zone 401 with said second attachment zone 402. The third attachment zone 403 may be a rear connecting attachment zone which connects a rear end portion of the first attachment zone 401 to a corresponding rear end portion of the second attachment zone 402. The U-shaped zone 401, 402, 403 guides the liquid from the left and right parts of the front portion to the rear portion. As illustrated the third attachment zone 403 may be arranged in the rear portion. In that manner a convenient liquid distribution channel network is created allowing the liquid to be distributed rapidly throughout the absorbent core.

FIG. 14 illustrates another exemplary embodiment of an absorbent article. The absorbent article further comprises an acquisition and distribution layer ADL 350 positioned between the absorbent core 300 and the liquid pervious topsheet 100. This serves to slow down the flow so that the liquid has adequate time to be absorbed by and evenly distributed over the absorbent core. The absorbent article may further comprise adhesive 360 between the absorbent core 300 and the ADL 350, and/or the absorbent article comprises adhesive 360 between the ADL and the liquid pervious topsheet 100.

FIGS. 15A and 15B illustrates an exemplary embodiment of an apparatus and a method for manufacturing an absorbent article according to an embodiment similar to the embodiment of FIGS. 2A and 2B but without the semi-permanent attachment zone. The method comprises:

preparing an absorbent core by providing a top core sheet 310 and a back core sheet 320, and by arranging absorbent material 330 partially between the top core sheet 310 and the back core sheet 320. The top core sheet 310 is attached to the back core sheet 320 forming two attachment zones, and the attaching is such that at least one of the top core sheet 310 and the back core sheet 320 has at least one edge portion having at least one free edge and covering a portion of the absorbent material; and including the absorbent core between a liquid pervious topsheet 100 and a liquid impervious backsheet 200.

The method may be carried out in detailed according to the steps described below.

In the embodiment of FIGS. 15A and 15B, the method comprises in a first step guiding a first sheet material, e.g. the top core sheet 310, along an optional guide roller 5, and further along a rotating member 10, wherein a surface of said rotating member 10 is provided with a pattern with suction zones 13 and non-suction zones 11. It is noted that a portion of the pattern of suction zones 13 and non-suction zones 11 is normally covered by the top core sheet 310, but for clarity purposes the top core sheet 310 is shown in a transparent manner to reveal the suction and non-suction zones 11, 13 of the rotating member 10. The suction zones 13 may be provided with holes, and the non-suction zones 11 are formed of closed material. For example, the non-suction zones 11 may be provided with inserts. The inserts may have a trapezoidal cross section. The inserts may be fixed e.g. with screws on the rotating member 10. At an inner area of the rotating member 10 a vacuum is applied, see VACUUM 1. The non-suction zones 11 may comprise at least one elongate zone 11 extending in a circumferential direction of the rotating member 10 in order to form at least one elongate attachment portion 400_a_, 400_b_. In the illustrated example a plurality of pairs of adjacent elongate non-suction zones are provided in order to form two elongate attachment portions 400_a_, 400_b_ in each absorbent core. In this step, a top core sheet 310 is provided.

In a second step an absorbent material 330 is applied via a hopper 40 on said top core sheet 310 on the rotating member 10. As a result, at least one attachment portion of the top core sheet 310 located above the non-suction zones 11 and remaining portions of the top core sheet 310 located above the suction zones 13 are covered with the absorbent material 330, wherein the absorbent material 330 is sucked towards the suction zones 13. However, some absorbent material 330 may remain on the non-suction zones 11.

Optionally, in a third step, the absorbent material 330 remaining on the at least one non-suction zone 11 may be locally removed, such that substantially no absorbent material 330 is present on the at least one attachment portion. The local removal of the absorbent material 330 may be done by a mechanical and/or pneumatic means. The removed absorbent material 330 may be discarded and/or collected and/or recycled by a further discharge means, such that the removed absorbent material can be further used. The discharge means preferably comprises a vacuum source to collect the removed absorbent material.

In a fourth step a second sheet material, e.g. the back core sheet 320 is applied on top of the absorbent material 330 on the top core sheet 310, e.g. using a further rotating member 15. In the this step, a back core sheet 320 is provided, such that absorbent material 330 is arranged partially between the top core sheet 310 and the back core sheet 320.

In a fifth step a third sheet material, e.g. the liquid impervious backsheet 200, is applied on top of the back core sheet 320, e.g. using a further rotating member 20. In this step, the liquid impervious backsheet 200 is provided.

In a sixth step the top core sheet 310 is attached to the back core sheet 320 at least in the at least one attachment portions, and such that two attachment zones are formed. The attaching may be done by applying pressure and/or heat on the top core sheet material 310 and/or on the back core sheet material 320 in the at least one attachment portion, e.g. by a rotating member 30 and/or opposite rotating member 30' which is provided with at least a first and a second seal rib 31, 32 dimensioned for applying pressure and/or heat on the top core sheet material 310 in the at least one attachment portion in order to create the two attachment zones. Additionally or alternatively adhesive may be applied to the back and/or top core sheets 310, 320, to release the bond between the top and back core sheets. In this step, two attachment zones 400a, 400b are formed by attaching the top core sheet 310 to the back core sheet 320, and the attaching is such that the top core sheet 310 has two edge portions each having a free edge and covering a portion of the absorbent material 330. The skilled person understands that this step may also be carried out before both the backsheet 200 and the topsheet 100 are provided or after both the backsheet 200 and the topsheet 100 are provided.

In a seventh step a fourth sheet material, e.g. the liquid pervious topsheet 100 is applied on top of the top core sheet 310, e.g. using a further rotating member 25. An adhesive 360 may be applied between the absorbent core and the liquid pervious topsheet 100. In this step, the absorbent core is included between a liquid pervious topsheet 100 and a liquid impervious backsheet 200.

In a possible embodiment, an acquisition and distribution layer ADL, is included between the absorbent core 300 and the liquid pervious topsheet 100. This serves to slow down the flow so that the liquid has adequate time to be absorbed by and evenly distributed over the absorbent core.

In a possible embodiment, adhesive is applied between the absorbent core 300 and the ADL, and/or between the ADL and the liquid pervious topsheet 100.

The top core sheet 310 and/or the back core sheet 320 can be any suitable material web which has sufficient strength to process through the apparatus, and preferably economically, environmentally and usage sensible. The top core sheet 310 and/or the back core sheet 320 may comprise a paper or fibrous tissue, woven or non-woven fabric, a cellulose web or batt, airlaid or wet laid structure or the like. Alternatively, the top core sheet 310 and/or the back core sheet 320 is a porous, gas permeable web material such as a porous film or fibrous web.

The top core sheet 310 and/or the back core sheet 320 may also be an essentially endless web material in the longitudinal direction. One preferred web material is a so called SMS material, comprising a spunbonded, a melt-blown and a further spunbonded layer. Highly preferred are permanently hydrophilic non-wovens, and in particular nonwovens with durably hydrophilic coatings. An alternative preferred material comprises a SMMS-structure. Another preferred web material is a nonwoven containing cellulosic fibers, paper or tissue sheet or other airlaid, drylaid or wetlaid material, as these products greatly improve the wicking capacity of the product. The top core sheet 310 and/or the back core sheet 320 may be provided from two or more separate sheets of materials or they may be alternatively provided from a unitary sheet of material. Preferred non-woven materials are provided from synthetic fibers, such as PE, PET and most preferably PP. As the polymers used for non-woven production are inherently hydrophobic, they are preferably coated with hydrophilic coatings.

The backsheet 200 prevents the bodily exudates absorbed by the absorbent core 300 and contained within the diaper from soiling other external articles that may contact the wearer, such as bed sheets and undergarments. In preferred embodiments, the backsheet 200 is substantially impervious to bodily exudates and comprises a laminate of a nonwoven and a thin plastic film such as a thermoplastic film. The backsheet 200 may comprise breathable materials that permit vapour to escape from the diaper while still preventing bodily exudates from passing through the backsheet 200. It may be semi-rigid, non-elastic and can be made fully or partially elasticized and include backing. The backsheet 200 may be assembled in a variety of well-known configurations and are well known in the art.

The topsheet 100 is preferably soft, compliant, exhibits good strikethroughs and has a reduced tendency to rewet from the liquid absorbent material. The topsheet 100 is placed in close proximity to the skin of the wearer when the diaper is worn. In this way, such topsheet 100 permits bodily exudates to rapidly penetrate it, so as to flow toward the absorbent core 300 more quickly, but preferably not allowing such bodily exudates to flow back through the topsheet 100. The topsheet 100 may be constructed from any one of a wide range of liquid and vapour permeable, preferably hydrophilic, materials. The upper and lower surface of the topsheet 100 may be treated differently and may for instance include a surfactant on the upper surface so as to facilitate liquid transfer there through, especially at a central zone or area of the topsheet 100 located over the absorbent core 300, and for instance include a hydrophobic agent on the lower surface to minimize the liquid contained within the absorbent core from contact wetting the topsheet 100 thereby reducing rewet values. The topsheet 100 may also be coated with a substance having rash preventing or rash reducing properties (e.g. aloe vera). The topsheet 100 covers substantially the entire wearer facing area of the diaper, including substantially all of the front waist region, back waist region, and crotch region. Further, the side panels and/or waist feature layers of the inner region may be formed from the same single top sheet material and, thus, may be referred to as being unitary with the topsheet 100 in forming longitudinal and lateral extensions of the topsheet material. Alternatively, the topsheet 100 may be formed from multiple different materials which vary across the width of the topsheet 100. Such a multiple piece design allows for creation of preferred properties and different zones of the topsheet 100. The topsheet 100 be semi-rigid, non-elastic and can be made fully or partially elasticized. The topsheet 100 may be assembled in a variety of well-known configurations and are well known in the art.

FIG. 16A, 16B, 16C illustrate schematically exemplary embodiments of methods for manufacturing an absorbent article. The top core sheet 310 and the back core sheet 320 may be fed continuously in a transport direction in the form of a web top core material and a web back core material having a first width w1, w1a and a second width w2, w2a, seen in a direction perpendicular on the transport direction, respectively; wherein the absorbent material 330 is arranged such that, seen in a direction perpendicular on the transport direction, a distance between outer limits of absorbent material is w0, wherein the distance w0 is larger than the first and/or the second width, preferably at least 10% larger, more preferably at least 20% larger, even more preferably at least 40% larger.

FIG. 16A illustrates schematically an exemplary embodiment of method for manufacturing an absorbent article. The top core sheet 310 and the back core sheet 320 are fed continuously in a transport direction in the form of a web top core material and a web back core material having a first width w1, and a second width w2, seen in a direction perpendicular on the transport direction, respectively. The absorbent material 330 is arranged such that, seen in a direction perpendicular on the transport direction, a distance between outer limits of absorbent material 330 is w0. The distance w0 is larger than the first width w1, preferably at least 10% larger, more preferably at least 20% larger, even more preferably at least 40% larger. In this particular embodiment, the distance w0 is at least 40% larger than the first width w1, the distance w0 and the second width w2 are within ±10% difference, preferably substantially the same.

The attaching may be such that a first edge portion 316 and a second edge portion 317 located at opposite sides of the attachment portion 315, having at least one free edge 313, 314 and covering a portion of the absorbent material, are formed. The first edge portion 316 and a second edge portion 317 may have a substantially similar width w3, and w3 is at least 1% of w0, preferably more than 3% of w0, even more preferably more than 5% of w0. This provides a stable structural basis for the formation of channel after the absorbent core is wetted, and results in the formation of tubes which provide a tub shape to the absorbent core. In the attachment zone 400 substantially no absorbent material is arranged between the top core sheet 310 and the back core sheet 320. The attachment zone 400 may be a continuous zone, which allows a better liquid distribution throughout the entire channel of the absorbent core 330, enabling better liquid absorbance. However, also a pattern of discrete attachments (e.g. dots, crosses, squares, etc.) may be used to form the attachment zone 400. In that regard it is noted that when the distance between the discrete attachments is small, e.g. lower than 1 cm or lower than 0.5 cm, a more or less continuous channel can be obtained upon wetting A rear and front edge of the top core sheet 310 may be attached to a rear and front edge of the back core sheet 320, respectively, which provides a more stable structure of the absorbent core while the use of material can still be reduced.

FIG. 16B illustrates schematically another exemplary embodiment of method for manufacturing an absorbent article. In this embodiment, the distance w0 is at least 40% larger than the second width w2, the distance w0 and the first width w1 are within ±10% difference, preferably substantially the same. The attaching may be such that the at least one attachment zone comprises a first attachment zone 400a and a second attachment zone 400b, which allows the creation of at least two channels using the at least one of the top core sheet 310 and the back core sheet 320. In this manner the quantity of liquid that can be temporarily held is further increased. In addition, as the total area of the attachment increases accordingly, the liquid can be more evenly distributed over the entire absorbent core. The first edge portion 326 and a second edge portion 327 may have a substantially similar width w3, and w3 is at least 1% of w0, preferably more than 3% of w0, even more preferably more than 5% of w0.

The attaching may be such that the first attachment zone 400a and the second attachment zone 400b extend next to each other from the crotch region in the direction of the first and/or the second transverse edge of the absorbent article, which allows a better liquid distribution between crotch region and front and/or back portion of absorbent article.

The attaching may be such that the first attachment zone 400a and the second attachment zone 400b are connected through at least one semi-permanent attachment zone, preferably extending in a substantially transverse direction, so that liquid can flow in a transverse direction through the absorbent material 330 of the absorbent core 300.

FIG. 16C illustrates schematically another exemplary embodiment of method for manufacturing an absorbent article, according to the embodiment of FIG. 6C. The method comprises providing a first top core sheet 310a, a first back core sheet 320a, a second top core sheet 310b and a second back core sheet 320b, and arranging absorbent material 330 partially between the first top core sheet 310a and the first back core sheet 320a, as well as between the second top core sheet 310b and the second back core sheet 320b. The first top core sheet 310a is attached to the first back core sheet 320a forming at a first attachment zone 400a, and the attaching is such that the first top core sheet 310a has two second edge portion 316a, 317a having at least one free edge 313a, 314a and covering a portion of the absorbent material. The second top core sheet 310b is attached to the second back core sheet 320b forming at a second attachment zone 400b, and the attaching is such that the second top core sheet 310b has two second edge portion 316b, 317b having at least one free edge 313b, 314b and covering a portion of the absorbent material. In this manner, two channels can be created with a reduced amount of material for manufacturing both the top core sheet and back core sheet, as a result the liquid distribution and absorption capacities of the absorbent core is further improved with a reduced manufacturing cost. The first width w1a and the second width w2a of the first top core sheet 310a and the first back core sheet 320a, respectively, are within ±10% difference, preferably substantially the same. And the first width w1b and the second width w2b of the second top core sheet 310b and the second back core sheet 320b, respectively, are within ±10% difference, preferably substantially the same. The distance w0 is larger than the sum of w1a+w1b (=w2a+w2b). The edge portions 316a, 317a, 316b, 317b may have a substantially similar width w3, and w3 is at least 1% of w0, preferably more than 3% of w0, even more preferably more than 5% of w0.

In addition, the providing is preferably such that a distance d1 between the first top core sheet 310a and the second top core sheet 310b is at least 5% of the width of the absorbent core w0, and/or a distance d2 between the back core sheet 320a and the second back core sheet 320b is at least 5% of the width of the absorbent core w0. In this manner a sufficient manufacturing cost reduction can be achieved.

FIGS. 17A and 17B illustrate another exemplary embodiment of an absorbent article comprising a liquid pervious topsheet 100, a liquid impervious backsheet 200, and an absorbent core 300 positioned between the liquid pervious topsheet 100 and the liquid impervious backsheet 200. The absorbent article has a first and second longitudinal edge 103, 104 and a first and second transverse edge 101, 102. The absorbent core 300 comprises a top core sheet 310, a back core sheet 320, and a layer of absorbent material 330 arranged partially between the top core sheet 310 and the back core sheet 320, such that the top core sheet 310 and the back core sheet 320 do not fully wrap the absorbent material. The top core sheet 310 comprises at least one attachment portion which is attached to the back core sheet 320 forming an attachment zone 400, and at least two edge portions 316, 317 covering a portion of the layer of absorbent material 330 on either side of the attachment zone 400. The edge portions 316, 317 each have an edge adjacent the attachment zone 400 and an opposite edge 313, 314 attached to the back core sheet 320, see attachment zones 600a, 600b which may be covered by absorbent material 330. Preferably the top sheet 100 is attached, e.g. using adhesive, to the absorbent material 330 on either side of the top core sheet 310 and/or to the top core sheet 310. By providing the top core sheet 310 such that it covers only a portion of a layer of absorbent material, the top core sheet 310 does not cover the entire top surface of the absorbent material 330, resulting in less raw material needed for the absorbent core 300. The attachment zone 400 is capable of creating a channel for liquid distribution and absorption upon wetting. In this manner, a channel can be created with a reduced amount of material used for manufacturing the top core sheet 310, and as a result the manufacturing cost can be reduced while good liquid distribution and absorption capacities can be maintained.

In the illustrated example of FIGS. 17A and 17B, the top core sheet 310 has a reduced width. However in other embodiments the back core sheet 320 may have a reduced width, or both 310, 320 may have a reduced width as has been illustrated above for embodiments with free edges.

Preferably, seen in a top view of the absorbent core, the top core sheet 310 has a total surface area of S1, the back core sheet 320 has a total surface area of S2, the absorbent core 300 has a surface area of S0 defined by an area covered by the absorbent material plus an area of the at least one attachment zone, wherein S1 is smaller than 90% of S0 and/or S2 is smaller than 90% of S0. S1 and/or S2 may be smaller than 80% of S0, preferably S1 and/or S2 may be smaller than 70% of S0, more preferably S1 and/or S2 may be smaller than 60% of S0, even more preferably S1 and/or S2 may be smaller than 50% of S0, most preferably S1 and/or S2 may be smaller than 40% of S0.

Preferably, in the at least one attachment portion 400 substantially no absorbent material is present between the top core sheet and the back core sheet. In the attachment zones 600a, 600b, absorbent material may be present.

The skilled person understands that the principles of the method illustrated in FIGS. 15A, 15B, 16A and 16B may also be used to produce an absorbent core as illustrated in FIGS. 17A and 17B, wherein additional attachment means may be provided to connect the edges 313, 314.

Although not illustrated in the figures, it is noted that one or more further discrete attachment zones, e.g. dot shaped attachment zones, may be provided, e.g. in a number of points along the free edges of the top and/or back core sheet to ensure that the top and back core sheet remain in a correct position with respect to each other. For example, in the embodiment of FIGS. 17A and 17B instead of providing the elongate attachment zones 600a, 600b there may be provided a plurality of discrete smaller attachment zones along the edges 313, 314, or in the corners of the top core sheet 310.

Whilst the principles of the invention have been set out above in connection with specific embodiments, it is to be understood that this description is merely made by way of example and not as a limitation of the scope of protection which is determined by the appended claims.

The invention claimed is:

1. An absorbent article comprising a liquid pervious topsheet, a liquid impervious backsheet, and an absorbent core positioned between the liquid pervious topsheet and the liquid impervious backsheet, said absorbent article having a first and second longitudinal edge and a first and second transverse edge;

wherein the absorbent core comprises a top core sheet, a back core sheet, and absorbent material arranged partially between the top core sheet and the back core sheet;

wherein the top core sheet and/or the back core sheet comprises a hydrophilic nonwoven;

wherein at least one of the top core sheet and the back core sheet comprises at least one attachment portion which is attached to the other one of the top core sheet and the back core sheet forming at least one attachment zone, and at least one edge portion having at least one free edge and covering a portion of the absorbent material.

2. The absorbent article of claim 1, wherein seen in a top view of the absorbent core, the top core sheet has a total surface area of S1, the back core sheet has a total surface area of S2, the absorbent core has a surface area of S0 defined by an area covered by the absorbent material plus an area of the at least one attachment zone, wherein S1 is smaller than 90% of S0 and/or S2 is smaller than 90% of S0.

3. The absorbent article of claim 2, wherein S1 and/or S2 is smaller than 80% of S0.

4. The absorbent article of claim 1, wherein in the at least one attachment zone substantially no absorbent material is present between the top core sheet and the back core sheet.

5. The absorbent article of claim 1, wherein the at least one edge portion comprises a first edge portion and a second edge portion located at opposite sides of the at least one attachment portion.

6. The absorbent article of claim 1, wherein the at least one attachment zone comprises an attachment zone extending from a crotch region in the direction of the first and/or second transverse edge of the absorbent core, and/or an attachment zone extending in the direction from the first longitudinal edge to the second longitudinal edge of the absorbent core.

7. The absorbent article of claim 1, wherein the top core sheet and/or the back core sheet has a substantially rectangular shape.

8. The absorbent article of claim 1, further comprising a second top core sheet comprising at least one second attachment portion which is attached to the back core sheet forming at least one second attachment zone, and at least one second edge portion having at least one free edge and covering a portion of the absorbent material.

9. The absorbent article of claim 1, further comprising a second top core sheet and a second back core sheet, said second top core sheet comprising at least one second attachment portion which is attached to the second back core sheet forming at least one second attachment zone, and at least one second edge portion having at least one free edge and covering a portion of the absorbent material.

10. The absorbent article of claim 1, further comprising a second back core sheet, said second back core sheet comprising at least one second attachment portion which is attached to the top core sheet forming at least one second attachment zone, and at least one second edge portion having at least one free edge and covering a portion of the absorbent material.

11. The absorbent article of claim 9, wherein a distance between the top core sheet and the second top core sheet is at least 5% of the width of the absorbent core; and/or wherein a distance between the back core sheet and the second back core sheet is at least 5% of the width of the absorbent core.

12. The absorbent article of claim 1, wherein the at least one attachment zone comprises at least one first attachment zone and at least one second attachment zone;

wherein preferably said at least one first and second attachment zones extend next to each other from the crotch region in the direction of the first and/or the second transverse edge; and/or wherein preferably said at least one first and second attachment zones are connected through at least one semi-permanent attachment zone, preferably extending in a substantially transverse direction.

13. The absorbent article of claim 1, wherein the absorbent article further comprises adhesive between the absorbent core and the liquid pervious topsheet; and/or wherein the absorbent article further comprises an acquisition and distribution layer positioned between the absorbent core and the liquid pervious topsheet; and/or wherein the absorbent article comprises adhesive between the absorbent core and the ADL, and/or the absorbent article comprises adhesive between the ADL and the liquid pervious topsheet.

14. The absorbent article of claim 1, wherein the top core sheet and/or the back core sheet has a longitudinal dimension which is at least 20% of a length of the absorbent core.

15. The absorbent article of claim 1, wherein the top core sheet and/or the back core sheet has a transverse dimension which is at least 5% of a width of the absorbent core; and/or wherein a longitudinal dimension of the top core sheet and/or the back core sheet and the length of the absorbent core are within +10% difference, preferably substantially the same; and/or wherein a transverse dimension of the top core sheet and/or a transverse dimension of the back core sheet and the width of the absorbent core are within +10% difference, preferably substantially the same; and/or wherein a rear and front edge of the top core sheet is attached to a rear and front edge of the back core sheet, respectively.

16. The absorbent article of claim 1, wherein the at least one attachment zone has a center line, preferably the center line is a straight line, or a curve, or a polyline; and/or wherein the at least one attachment zone comprises a plurality of attachments zones which have substantially no absorbent material between the top core sheet and the back core sheet, and wherein absorbent material is present in an area in-between said plurality of attachment zones, between the top core sheet and the back core sheet; and/or wherein a contour of the or each attachment zone is adjacent to absorbent material; and/or wherein a length of the or each attachment zone is larger than 10% of the length of the absorbent core.

17. The absorbent article of claim 1, wherein said at least one attachment zone comprises at least one permanent attachment zone which remains attached when wetted.

18. The absorbent article of claim 1, wherein the absorbent material comprises cellulosic fluff pulp and/or superabsorbent particles.

19. An absorbent article comprising a liquid pervious topsheet, a liquid impervious backsheet, and an absorbent core positioned between the liquid pervious topsheet and the liquid impervious backsheet, said absorbent article having a first and second longitudinal edge and a first and second transverse edge;

wherein the absorbent core comprises a top core sheet, a back core sheet, and absorbent material arranged partially between the top core sheet and the back core sheet;

wherein at least one of the top core sheet and the back core sheet comprises at least one attachment portion which is attached to the other one of the top core sheet and the back core sheet forming at least one attachment zone, the absorbent article further comprising a second top core sheet and a second back core sheet, said second top core sheet comprising at least one second attachment portion which is attached to the second back core sheet forming at least one second attachment zone.

20. The absorbent article of claim 19, wherein the absorbent article further comprises an acquisition and distribution layer, ADL, positioned between the absorbent core and the liquid pervious topsheet.

* * * * *